United States Patent [19]

Sakashita et al.

[11] Patent Number: 5,149,462
[45] Date of Patent: Sep. 22, 1992

[54] OPTICALLY ACTIVE COMPOUND

[75] Inventors: Keiichi Sakashita; Seiji Hayashi; Tetsuya Ikemoto, all of Kawasaki; Osamu Yamamoto, Tokyo, all of Japan

[73] Assignee: Mitsubishi Rayon Company Ltd., Tokyo, Japan

[21] Appl. No.: 551,898

[22] Filed: Jul. 12, 1990

[30] Foreign Application Priority Data

Jul. 12, 1989 [JP] Japan ................................. 1-179867

[51] Int. Cl.⁵ ..................... C09K 19/34; C07D 309/00
[52] U.S. Cl. .................................. 252/299.61; 549/273
[58] Field of Search ....................... 252/299.61, 299.65; 549/273

[56] References Cited

U.S. PATENT DOCUMENTS 4,576,732  3/1986  Isogai et al. ..................... 252/299.65
4,818,431  4/1989  Eidenschink et al. ......... 252/299.61

FOREIGN PATENT DOCUMENTS 0117476  9/1984  European Pat. Off. .
0313379  4/1989  European Pat. Off. .
0396410  11/1990 European Pat. Off. .

OTHER PUBLICATIONS

Patent Abstracts of Japan, vol. 13, No. 501 (C-652) [3849], Nov. 10, 1989, p. 107 C 652; & JP-A-1 199959 (Mitsubishi Rayon Co., Ltd) Nov. 8, 1989 *Abstract*.

Primary Examiner—Robert L. Stoll
Assistant Examiner—C. Harris
Attorney, Agent, or Firm—Oblon, Spivak, McClelland, Maier & Neustadt

[57] ABSTRACT

Disclosed is an optically active compound represented by the formula:

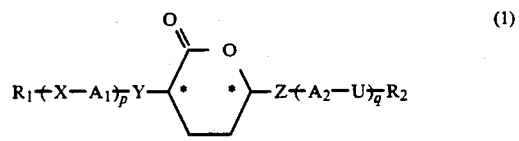

wherein $R_1$ and $R_2$ are alkyl, alkenyl or alkoxy-alkyl, which may be substituted by halogen, X and U are a direct bond, —O—, —COO— or —OCO—, Y and Z are a direct bond, —COO—, —OCO—, —CH$_2$O— or —OCH$_2$—, $A_1$ and $A_2$ are phenylene, cyclohexylene or a phenylene- or cyclohexylene-containing group, p and q are 0 or 1, C* is an asymmetric carbon atom, with the proviso that when Z is a direct bond, q is 0, $R_2$ is alkyl, Y is a direct bond, —OCO— or —OCH$_2$—. The optically active compound is used as a ferroelectric liquid crystal or an additive to a ferroelectric or non-ferroelectric liquid crystal.

1 Claim, No Drawings

OPTICALLY ACTIVE COMPOUND

BACKGROUND OF THE INVENTION

(1) Field of the Invention

The present invention relates to a novel optically active compound having a δ-valerolactone ring in the structure.

(2) Description of the Related Art

Liquid crystals currently used in a liquid crystal display (LCD) are classified into the one exhibiting nematic phase, and since they are of the light-receiving type, they are characterized in that there is no eye fatigue therefrom and the power consumption is very small. Nevertheless, these liquid crystals have problems in that the response speed is low and the view angle of the display is narrow.

Display devices and printer heads using a ferroelectric liquid crystal having advantageous characteristics similar to those of the nematic liquid crystal such as the property of not fatiguing eyes and the small power consumption, and having a high response speed and high contrast characteristics comparable to those of a light-emitting type display element have been investigated.

The discovery of the ferroelectric liquid crystal was reported for the first time by R. B. Meyer et al [J. Physique, 36, L-69 (1975)]. This ferroelectric liquid crystal is classified into that exhibiting a chiral smectic C phase (hereinafter referred to as "Sm*C phase"). A typical example of the ferroelectric liquid crystal is p-decyloxybenzylidene-p'-amino-2-methylbutyl cinnamate (hereinafter referred to as "DOBAMBC") represented by the following formula:

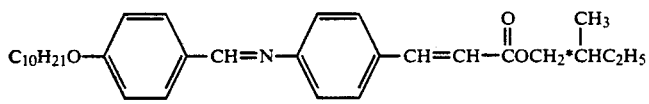

In DOBAMBC and most of the ferroelectric liquid crystals proposed thereafter, the range of temperatures showing the ferroelectric property (the range of temperatures wherein the Sm*C phase is present) is very narrow, and these liquid crystal materials cannot be practically used alone. Therefore, attempts have been made to expand the range of temperatures showing the Sm*C phase to the lower and higher temperature sides, taking room temperature as the center, by mixing a variety of ferroelectric liquid crystals. A ferroelectric liquid crystal having a larger spontaneous polarization than heretofore proposed ferroelectric liquid crystals is desired for a printer head for which a very short response time is required.

SUMMARY OF THE INVENTION

A primary object of the present invention is to provide an optically active compound which is chemically stable, is not colored and has a good light stability and which gives a liquid crystal composition having a large spontaneous polarization when the optically active compound is incorporated in a liquid crystal composition.

In accordance with the present invention, there is provided an optically active compound having a δ-valerolactone ring, which is represented by the following formula (1):

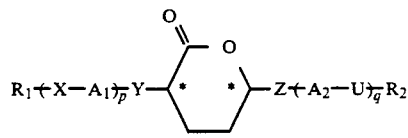

wherein $R_1$ and $R_2$ independently represent a linear or branched alkyl group having 1 to 18 carbon atoms, a linear or branched alkenyl group having 2 to 18 carbon atoms, a linear or branched alkoxyalkyl group having 1 to 3 carbon atoms in the alkoxy portion and 1 to 18 carbon atoms in the alkyl portion, or an alkyl, alkenyl or alkoxyalkyl group as mentioned above in which at least one hydrogen atom is substituted by a halogen atom, with the proviso that when $R_1$ or $R_2$ has a structure that can possess an optically active group, it may be an optically active group or a racemic modification, X and U independently represent a direct bond, —O—,

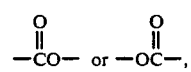

Y and Z independently represent a direct bond,

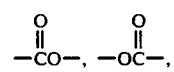

—CH$_2$O— or —OCH$_2$—, $A_1$ and $A_2$ independently represent

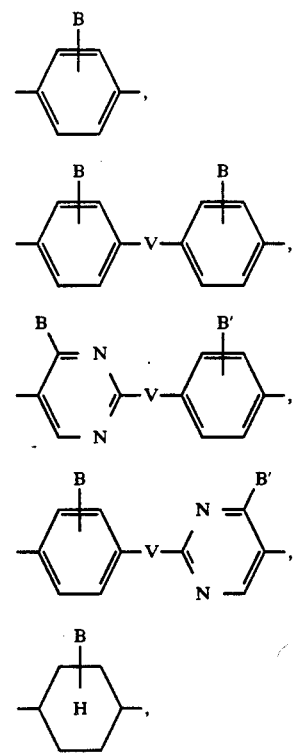

-continued

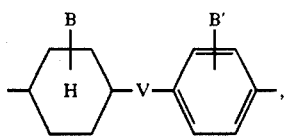
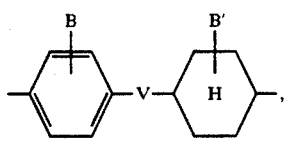
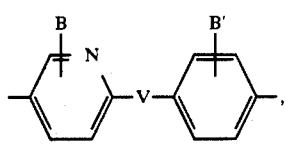
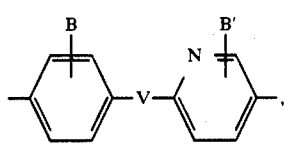
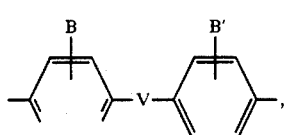
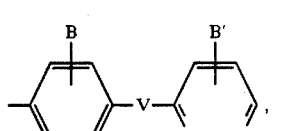
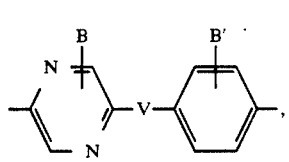
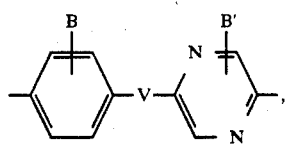
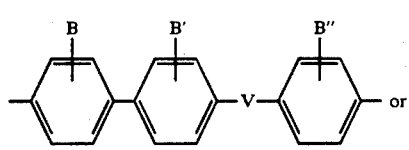 or
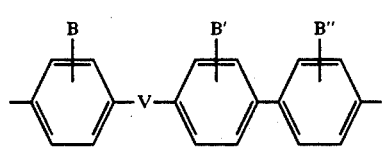

in which B, B' and B" independently represent a hydrogen atom, a halogen atom, a cyano group, a methyl group, a methoxy group or a trihalomethyl group and V represents a direct bond, $-CH_2O-$, $-OCH_2-$,

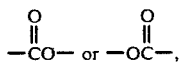

p and q independently represent 0 or 1, and *C represents an asymmetric carbon atom, with the proviso that when Z is a direct bond, q is 0 and $R_2$ is a linear alkyl group, Y represents a direct bond,

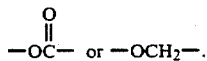

or $-OCH_2-$.

DESCRIPTION OF THE PREFERRED EMBODIMENTS

In the optically active compound of the present invention, $R_1$ and $R_2$ in the general formula (1) are preferably a linear or branched alkyl group having 4 to 14 carbon atoms, a linear or branched alkenyl group having 4 to 14 carbon atoms, or a linear or branched alkoxyalkyl group having 4 to 14 carbon atoms in the alkyl group. As the linear alkyl group, there can be mentioned, for example, an n-butyl group, an n-pentyl group, an n-hexyl group, an n-octyl group, an n-nonyl group, an n-decyl group, an n-dodecyl group and an n-tetradecyl group. As the branched alkyl group, there can be mentioned methyl-branched alkyl groups represented by the following formula:

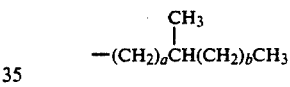

wherein a is an integer of from 0 to 10 and b is an integer of from 1 to 11, with the proviso that the condition of $1 \leq (a+b) \leq 11$ is satisfied.

These methyl-branched alkyl groups may be optically active groups, or racemic modifications, and all thereof are preferably used.

As the halogen-substituted alkyl group, there can be mentioned groups represented by the following formula:

wherein W represents fluorine, chlorine or bromine, and k and i independently represent an integer of from 0 to 12, with the proviso that the condition $2 \leq (k+i) \leq 12$ is satisfied.

These groups are preferably optically active groups.

As the halogen-substituted branched alkyl group, there can be mentioned alkyl groups having a trifluoromethyl branch, represented by the following formula:

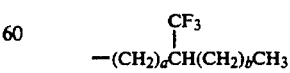

wherein a and b are as defined above. Also these groups are preferably optically active groups.

As the linear alkoxyalkyl group, there can be mentioned groups represented by the following formula:

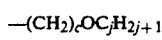

wherein c is an integer of from 4 to 14 and j is an integer of from 1 to 3,
and as the branched alkoxyalkyl group, there can be mentioned groups represented by the following formulae:

$$-(CH_2)_k\overset{CH_3}{\underset{|}{CH}}(CH_2)_j OC_jH_{2j+1}$$

and $$-(CH_2)_k\overset{OC_jH_{2j+1}}{\underset{|}{CH}}(CH_2)_j CH_3$$

wherein i, j and k are as defined above. The branched alkoxylalkyl groups may be racemic modifications or optically active groups.

As the groups $A_1$ and $A_2$ in the formula (1), the following groups can be mentioned:

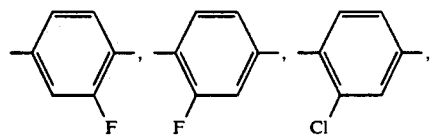

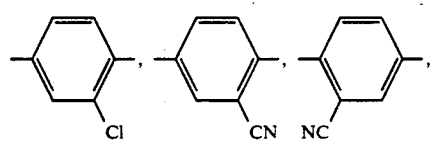

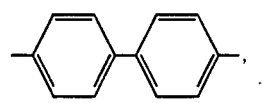

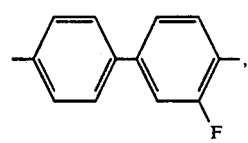

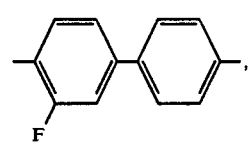

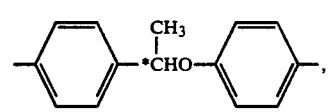

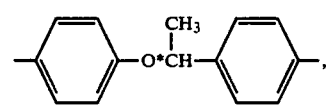

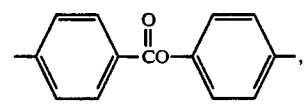

-continued

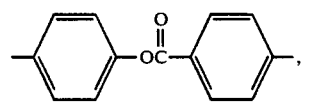

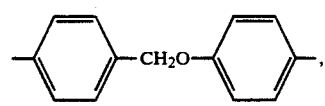

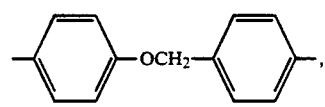

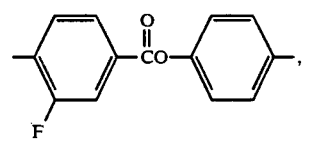

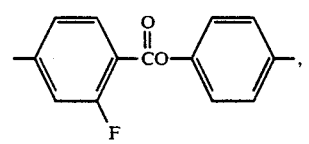

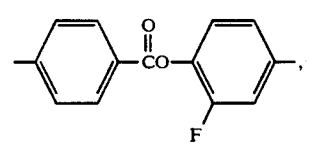

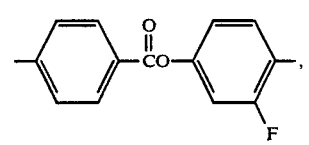

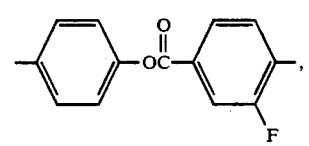

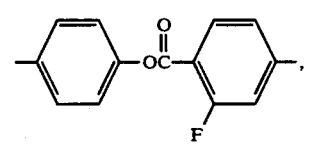

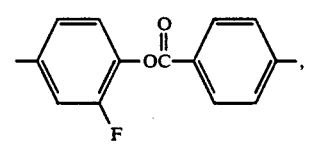

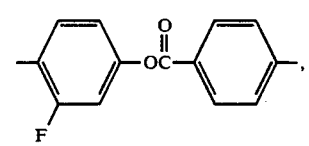

-continued
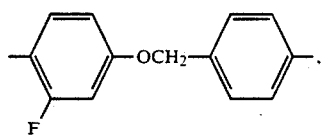
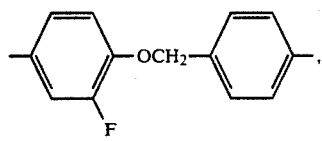
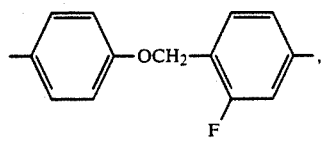
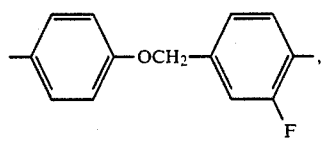
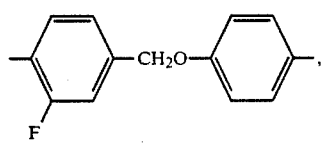
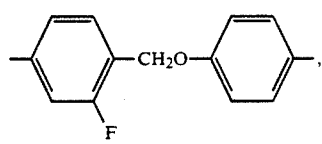
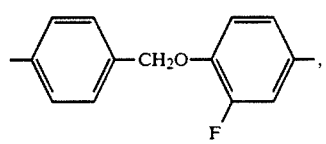
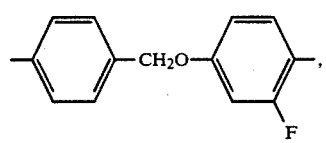
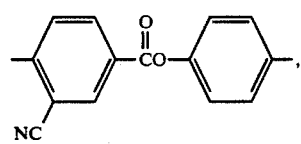
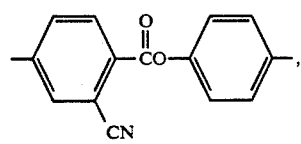
-continued
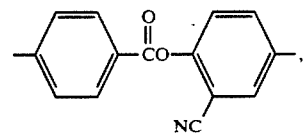
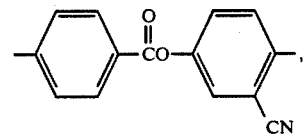
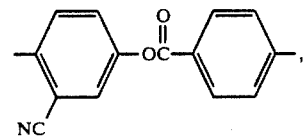
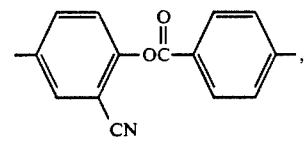
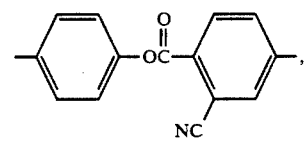
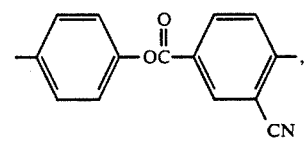
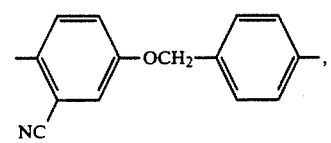
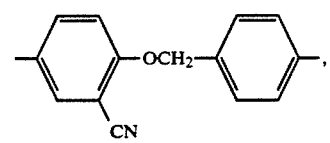
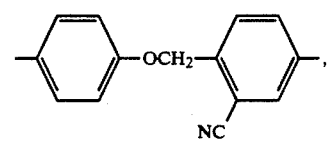
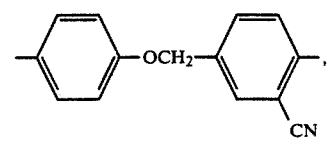

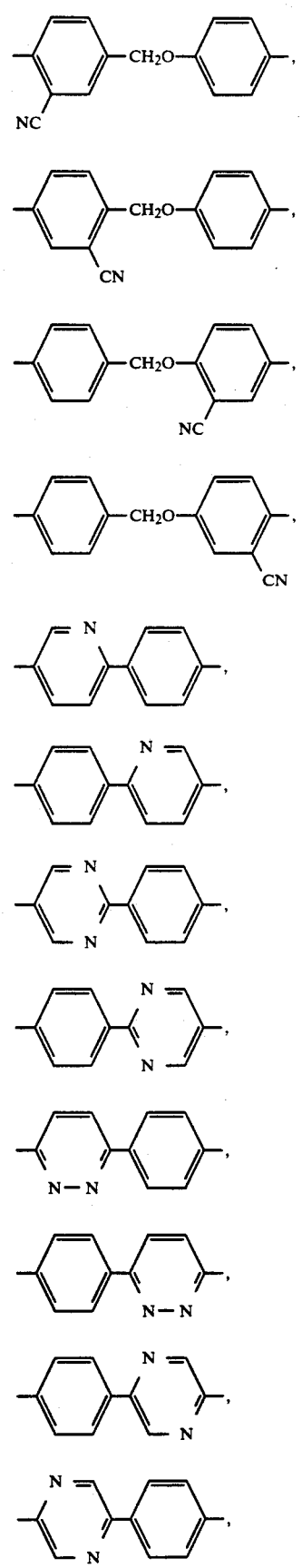
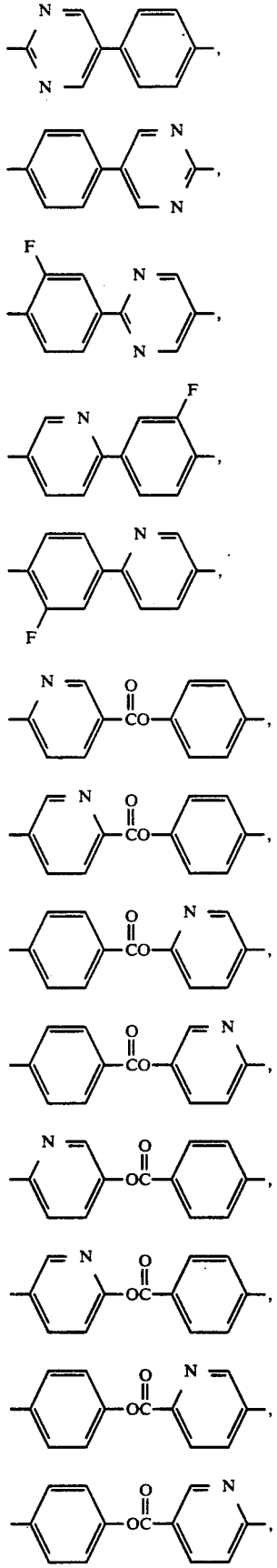

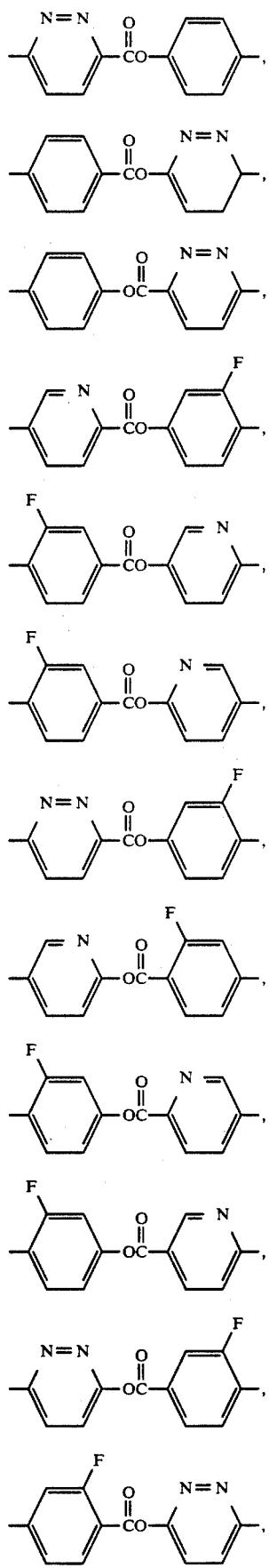

-continued
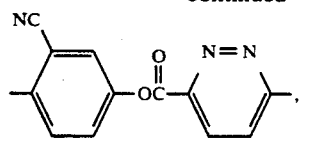
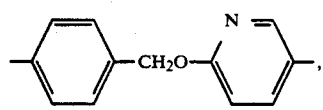
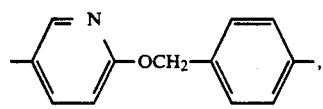
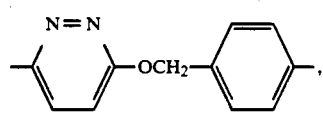
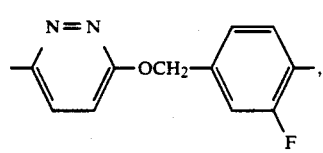
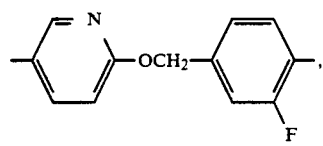
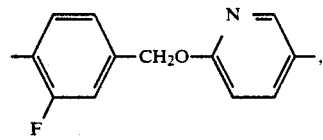
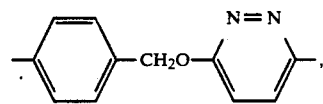
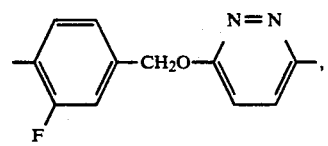
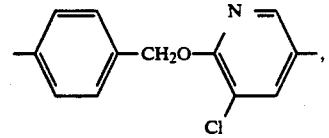
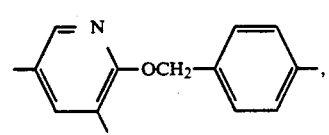
-continued
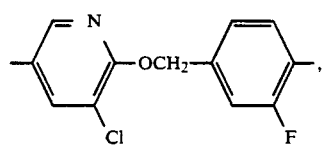
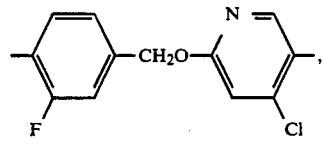
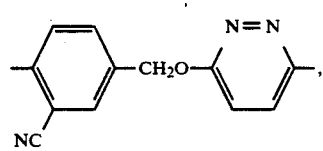
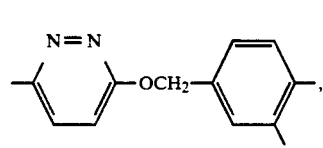
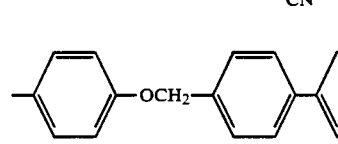
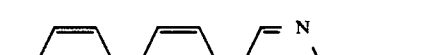
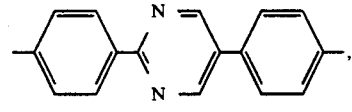
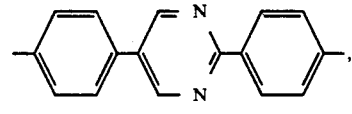
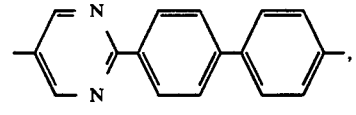
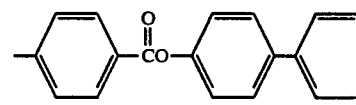
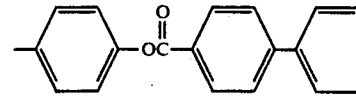

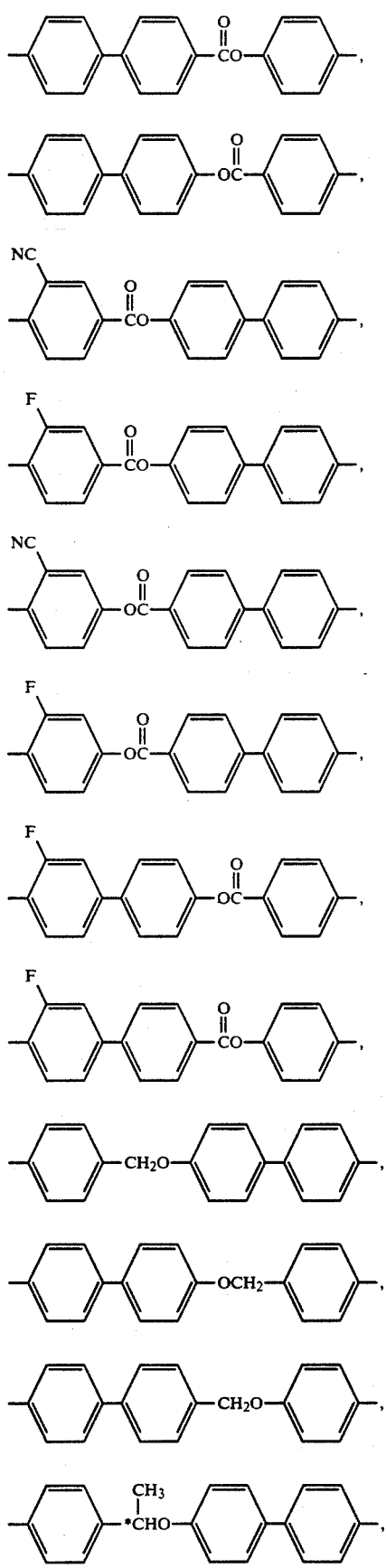

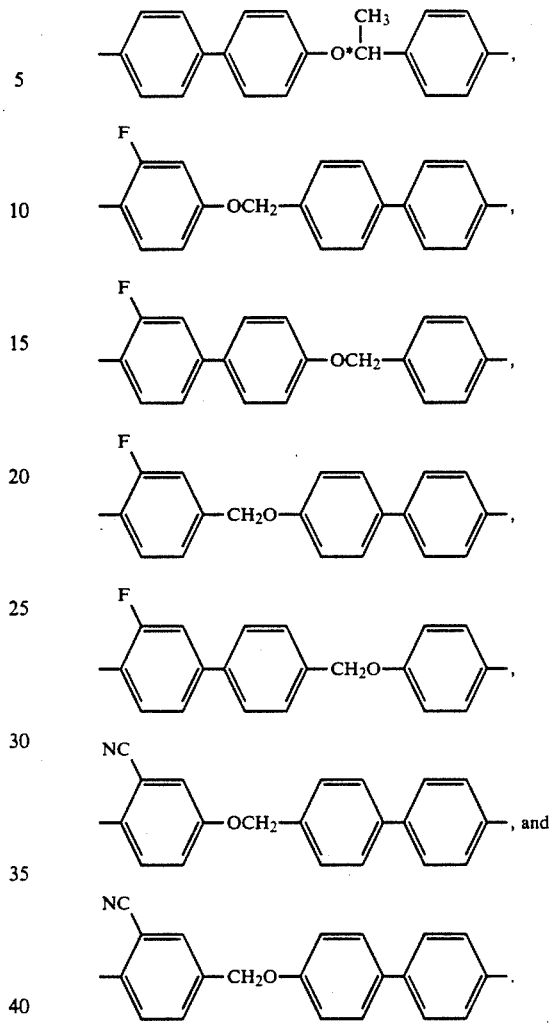

To increase the response speed of a liquid crystal composition comprising the optically active compound, preferably the dipole moment of the asymmetric carbon atom is increased or the rotational hindrance around the asymmetric carbon atom is increased. Accordingly, Y and Z in the general formula (1) preferably represent a direct bond

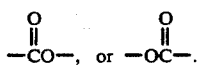

In view of the molecular linearity of the ease of the appearance of the tilted liquid crystal phase by the induced dipole moment, Y and Z preferably represent

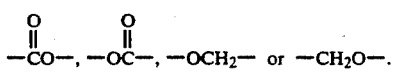

In view of the ease of the synthesis, Y and Z preferably represent a direct bond,

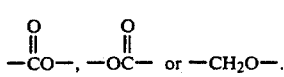

In view of the ease of the synthesis, X and U preferably represent —O—,

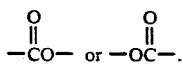 or 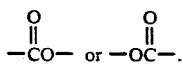.

In view of the size of the dipole moment, the rotational hindrance and the ease of the appearance of the tilted liquid crystal phase, V is preferably

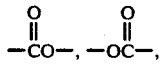,

—OCH$_2$— or —CH$_2$O—, and in view of the ease of the synthesis, V is preferably a direct bond,

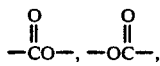,

—OCH$_2$— or —CH$_2$O—.

Compounds of the general formula (1) can be prepared according to the following processes.

Compounds where Y is

,

Z is a direct bond, and each of p and q is 1:

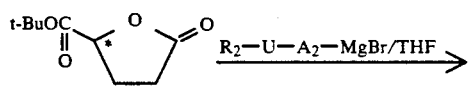

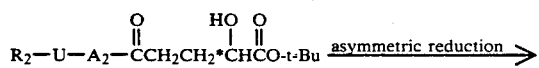

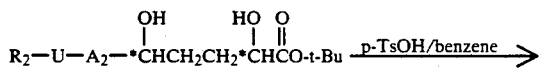

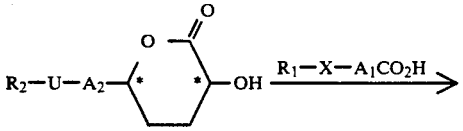

Compounds in which each of Y and Z is a direct bond, p is 0 and q is 1:

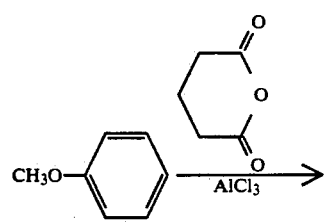

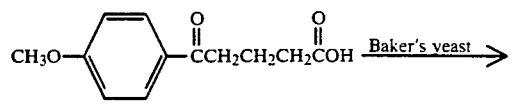

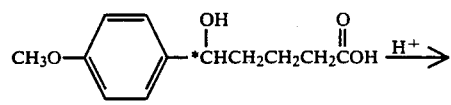

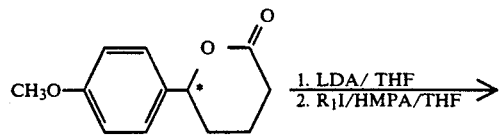

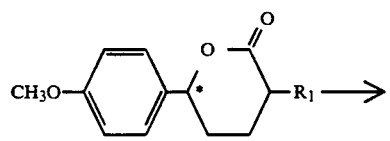

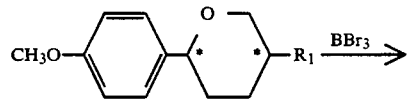

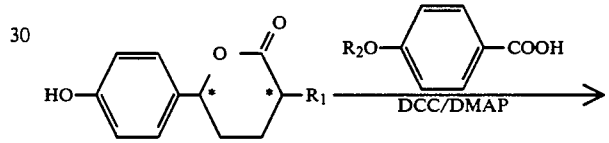

Compounds in which each of Y and Z is a direct bond and each of p and q is 1:

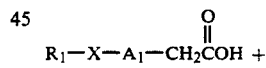

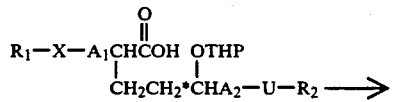

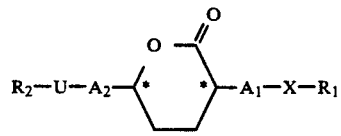

Compounds in which Y is

,

Z is a direct bond and each of p and q is 1:

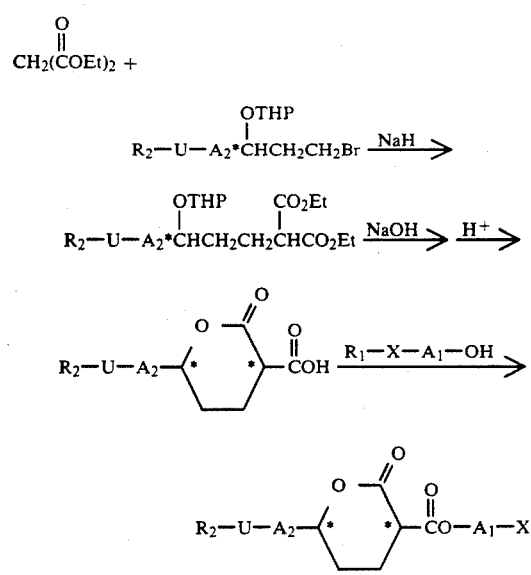
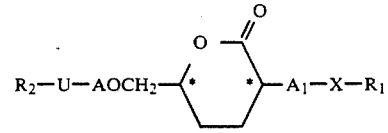
Compounds in which Y is a direct bond, Z is
$$-\overset{O}{\underset{\|}{C}}O-$$
and each of p and q is 1:
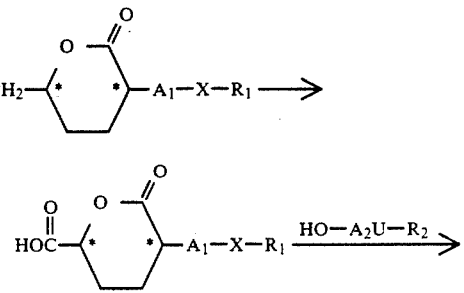
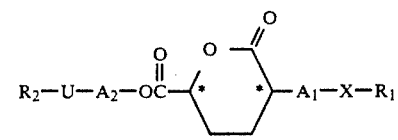
Compounds in which Y is —OCH$_2$—, Z is a direct bond and each of p and q is 1:
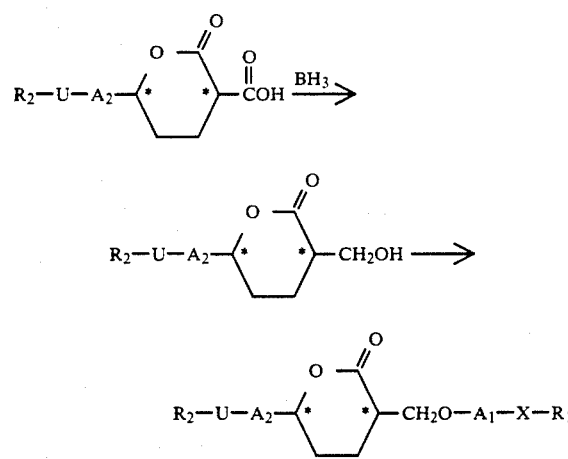
Compounds in which Y is a direct bond, Z is —CH$_2$O— and each of p and q is 1:
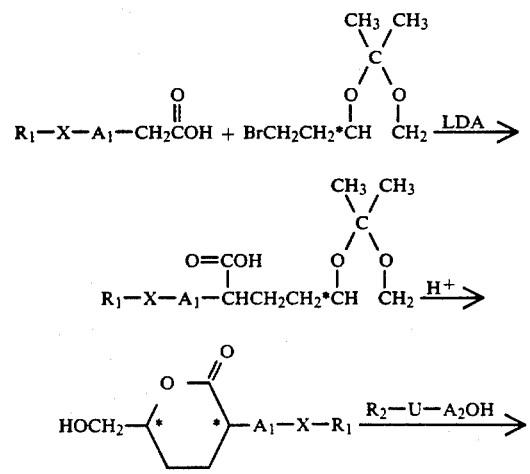
Compounds in which Y is
$$-\overset{O}{\underset{\|}{C}}O-,$$
Z is —CH$_2$O— and each of p and q is 1:
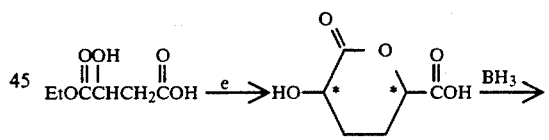
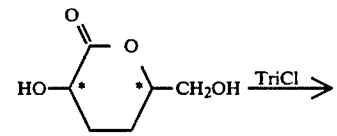
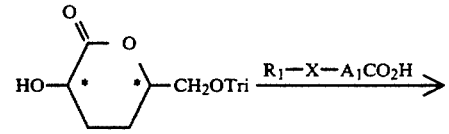
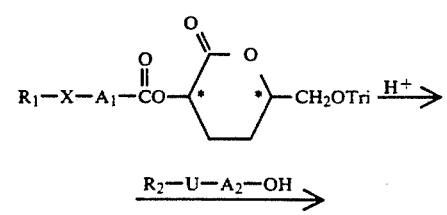

-continued

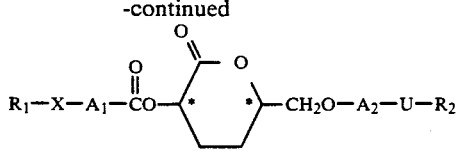

Compounds in which Y is

Z is —CH$_2$O— and each of p and q is 1:

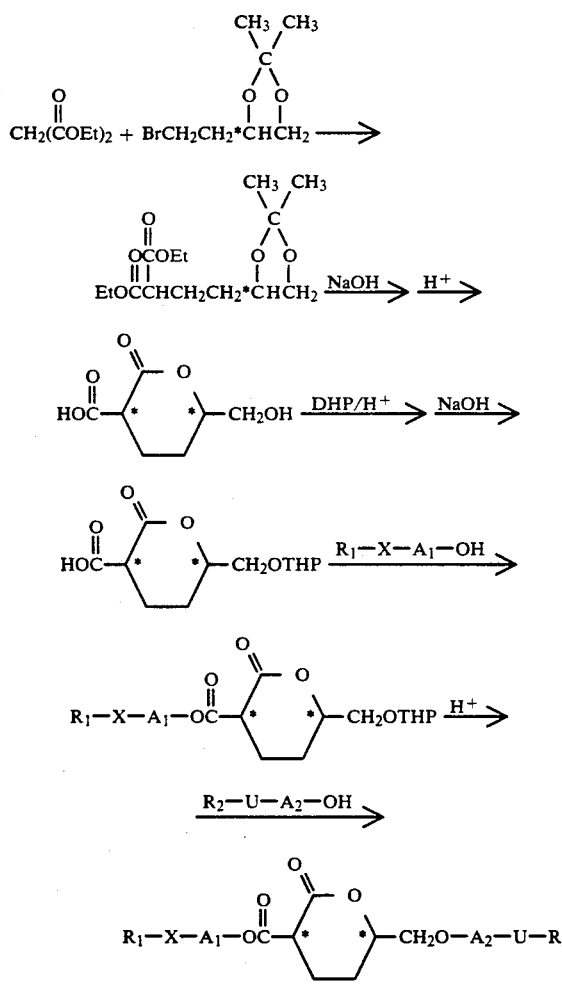

It is considered that a large dipole moment, which is restricted in its rotation around the asymmetric carbon atom, makes the greatest contribution to the manifestation of a spontaneous polarization or latent spontaneous polarization. It also is considered that, if the number of asymmetric carbon atoms is increased, a rotation of the molecule along the long axis of the molecule is restricted and the order parameter of the orientation of the permanent dipole moment is increased, and that this also makes a contribution to the manifestation of a spontaneous polarization or latent spontaneous polarization.

The optically active compound represented by the general formula (1) has two asymmetric carbon atoms fixed by the δ-valerolactone ring, and the permanent dipole moment derived from the lactone linkage is fixed by the δ-valerolactone ring which can be regarded as a part of the mesogene. Accordingly, the compound of the present invention is characterized in that a spontaneous polarization or a latent spontaneous polarization is large.

Some of the optically active compounds included within the scope of present invention do not show a liquid crystalline phase, though other compounds of the present invention show a liquid crystalline phase. Even a compound not showing a liquid crystalline phase has such a property, if the compound is incorporated into a non-chiral liquid crystal or liquid crystal composition showing the phase series of isotropic phase-nematic phase-smectic A phase or isotropic phase-nematic phase-smectic C phase in an amount not destroying the liquid crystallinity, that is, 1 to 90 mole %, the ferroelectric liquid crystalline phase (chiral smectic C phase) is induced.

Accordingly, even a compound not showing the liquid crystal phase is valuable as an additive to a ferroelectric liquid crystal composition.

Where a liquid crystal is used for the display or the like, a composition comprising a plurality of liquid crystal compounds is advantageous over liquid crystal consisting of a single liquid crystal compound, because the applicable temperature ranges (the temperature showing the ferroelectric characteristic), the tilt angle, the helical pitch, the spontaneous polarization value, the rotational viscosity, and other physical properties can be voluntarily changed.

The liquid crystal composition of the present invention comprises at least one optically active compound represented by the general formula (1). As the component to be mixed with this optically active compound, there can be mentioned ferroelectric liquid crystal compounds and compositions, and non-chiral liquid crystal compounds and liquid crystal compositions as mentioned above. For example, the following compounds can be preferably mixed with the optically active compound represented by the general formula (1):

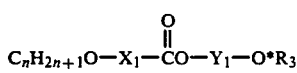

wherein n = 7-12, X$_1$ = 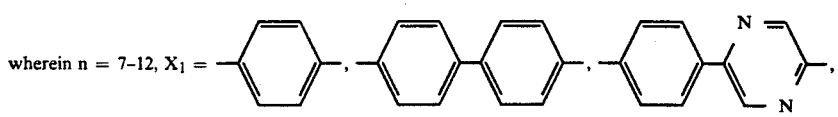

-continued

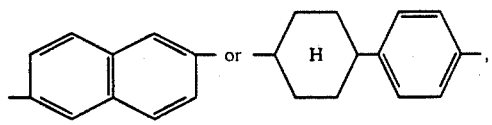

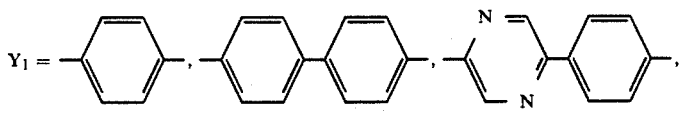

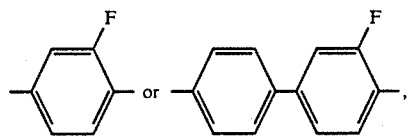

*R₃ = —CH₂*$\overset{CH_3}{C}$HC₂H₅, —CH₂*$\overset{Cl}{C}$HC₂H₅, —CH₂*$\overset{Br}{C}$HC₂H₅, —CH₂*$\overset{CH_3}{C}$HC₃H₇, —CH₂*$\overset{F}{C}$HC$_m$H$_{2m+1}$ (m = 5, 6, 8, 10 or 12), —(CH₂)₂*$\overset{CF_3}{C}$HC₄H₉, —(CH₂)₃*$\overset{CH_3}{C}$HC₂H₅, —(CH₂)₃*$\overset{CH_3}{C}$HC₃H₇, —CH₂*$\overset{CH_3}{C}$HOC₁₂H₂₅, —(CH₂)₃*$\overset{CH_3}{C}$HOC₅H₁₁, —(CH₂)₅*$\overset{CH_3}{C}$HOC₅H₁₁, —*$\overset{CH_3}{C}$HCOC₅H₁₁ or —CH₂*$\overset{CH_3}{C}$HCOC₄H₉;
           $\quad\quad\quad\quad\quad\quad\quad\quad\quad\quad\quad\quad\quad\quad\quad\quad\quad\quad\quad\quad\quad$ ‖     $\quad\quad\quad\quad\quad\quad\quad\quad\quad$ ‖
           $\quad\quad\quad\quad\quad\quad\quad\quad\quad\quad\quad\quad\quad\quad\quad\quad\quad\quad\quad\quad\quad$ O    $\quad\quad\quad\quad\quad\quad\quad\quad\quad$ O $C_nH_{2n+1}O—X_2—O\overset{O}{\overset{\|}{C}}—Y_2—O^*R_4$

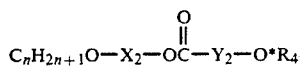

wherein n = 6, 8 or 10, X₂ =

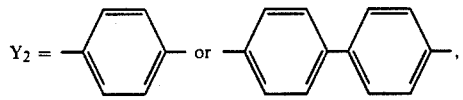

Y₂ =

*R₄ = —CH₂*$\overset{CH_3}{C}$HC₂H₅, —*$\overset{CH_3}{C}$HC₆H₁₃, —(CH₂)₃*$\overset{CH_3}{C}$HC₂H₅, —CH₂*$\overset{CH_3}{C}$HCH(CH₃)₂, —CH₂*$\overset{F}{C}$HC₈H₁₇, —CH₂*$\overset{CH_3}{C}$HOC₅H₁₁, —*$\overset{CH_3}{C}$HCOC₈H₁₇ or —$\overset{CH_3}{C}$*$\overset{}{C}$HOC₈H₁₇;
          $\quad\quad\quad\quad\quad\quad\quad\quad\quad\quad\quad\quad\quad\quad\quad\quad\quad\quad\quad\quad\quad\quad$ ‖     $\quad\quad\quad\quad\quad\quad\quad\quad\quad$ ‖
          $\quad\quad\quad\quad\quad\quad\quad\quad\quad\quad\quad\quad\quad\quad\quad\quad\quad\quad\quad\quad\quad\quad$ O    $\quad\quad\quad\quad\quad\quad\quad\quad\quad$ O $C_nH_{2n+1}—X_3—\overset{O}{\overset{\|}{C}}—O—Y_3—O^*R_5$

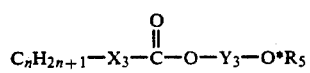

wherein n = 3, 7 or 8, X₃ =

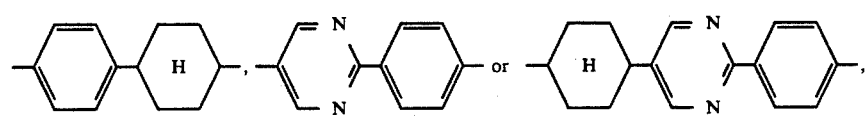

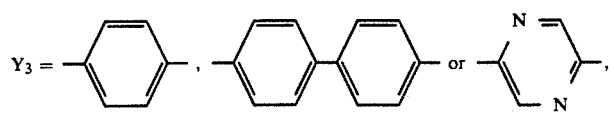

Y₃ =

*R$_5$ = —CH$_2$*CHC$_m$H$_{2m+1}$ (m = 2 or 6) or —CH$_2$*CHC$_m$H$_{2m+1}$ (m = 5, 6 or 8, Z$_1$ = F or Cl), with CH$_3$ and Z$_1$ substituents respectively;

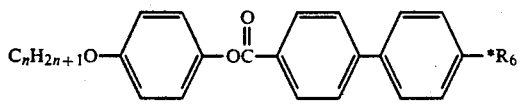

wherein n = 8, 10, 12 or 16, *R$_6$ = —CH$_2$*CHC$_2$H$_5$, —OCH$_2$*CHC$_2$H$_5$, —OCH$_2$*CHC$_3$H$_7$ (with CH$_3$ substituents), —OCH$_2$*CHC$_8$H$_{17}$ (with F substituent), —OCH$_2$*CHOC$_4$H$_9$ or —OCH$_2$*CHOC$_8$H$_{17}$ (with CH$_3$ substituents);

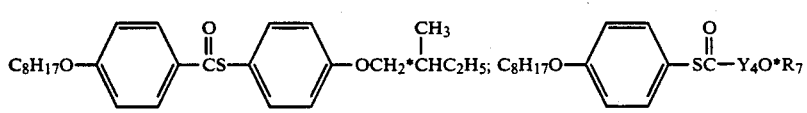
C$_8$H$_{17}$O—⌬—S(=O)C—⌬—OCH$_2$*CHC$_2$H$_5$ (CH$_3$); C$_8$H$_{17}$O—⌬—SC(=O)—Y$_4$O*R$_7$ wherein Y$_4$ = —⌬—⌬— or —⌬—,

*R$_7$ = —CH$_2$*CHOC$_5$H$_{11}$ (CH$_3$) or —CH$_2$*CHC$_6$H$_{13}$ (F); C$_n$H$_{2n+1}$O—X$_4$—CO—Y$_5$—CO*R$_8$ (with =O on both carbonyls)

wherein n = 5-8, 10 or 12, X$_4$ and Y$_5$ = —⌬—, —⌬—⌬— or

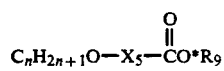, with the proviso that at least one of X$_4$ and Y$_5$ is —⌬—,

*R$_8$ = —CH$_2$*CHC$_2$H$_5$ (CH$_3$), —CH$_2$*CHC$_6$H$_{13}$ (F), —*CHC$_8$H$_{17}$ (CN), —CH$_2$*CHOC$_5$H$_{11}$ (CH$_3$),

—(CH$_2$)$_5$*CHOC$_5$H$_{11}$ (CH$_3$), —*CHC$_6$H$_{13}$ (CF$_3$), —*CHOC$_2$H$_5$ (CH$_3$) or —*CHCH$_2$COC$_2$H$_5$ (CF$_3$, =O);

C$_n$H$_{2n+1}$O—X$_5$—C(=O)O*R$_9$ wherein n = 5, 7, 8 or 12, X$_5$ = —⌬—⌬—, pyrimidine-phenyl, —H—⌬—⌬—, —H—pyrimidine-phenyl or —⌬—pyrimidine—,

*R$_9$ = —(CH$_2$)$_3$*CHC$_2$H$_5$ (CH$_3$), —CH$_2$*CHC$_6$H$_{13}$ (F), —CH$_2$*CHC$_8$H$_{17}$ (F) or —*CHC$_8$H$_{17}$ (CN);

R$_1$'—X$_6$—O*R$_{10}$ wherein R$_1$' = —C$_8$H$_{17}$, —C$_9$H$_{19}$, —C$_{10}$H$_{21}$, —OC$_{10}$H$_{21}$ or —C$_{11}$H$_{23}$,

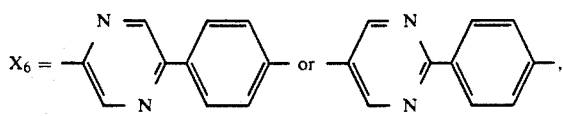

*$R_{10} = -(CH_2)_5*CHC_2H_5, -(CH_2)_3*CHC_2H_5, -(CH_2)_2*CHC_2H_5, -(CH_2)_3*CHOC_5H_{11}, -(CH_2)_5*CHOC_5H_{11}$, (each with CH₃ branch)

$-(CH_2)_3*CHOC_3H_7, -(CH_2)_2*CHOC_{12}H_{25}, -CH_2*CHOC_3H_7, -CH_2*CHC_6H_{13}, -CH_2*CHC_8H_{17}$, (first three with CH₃ branch, last two with F branch)

$-(CH_2)_2*CHC_2H_5, -(CH_2)_2OCH_2*CHC_2H_5, -CH_2OCH_2*CHC_8H_{17}$, or $-(CH_2)_4OCH_2*CHC_6H_{13}$;

(with Cl, CN, F, F branches respectively)

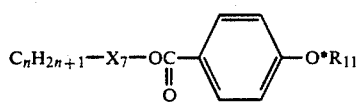

$C_nH_{2n+1}-X_7-OC(=O)-\phenyl-O*R_{11}$ wherein n = 8, 10 or 12, $X_7 =$ 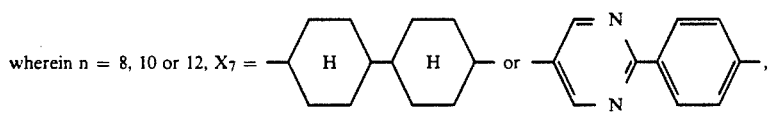

*$R_{11} = -(CH_2)_3*CHC_2H_5, -(CH_2)_2*CHC_2H_5, -(CH_2)_2*CHC_2H_5, -CH_2*CHC_6H_{13}$ or $-CH_2*CHC_4H_7$;

(with CH₃, CH₃, Cl, F, F branches)

$R_2'-X_8-OCH_2Y_6-*R_{12}$ wherein $R_2' = -C_2H_5, -C_{10}H_{21}, -OC_6H_{13}, -OC_7H_{15}, -OC_8H_{17}, -OC_{10}H_{21}$ or $-OC_{12}H_{25}$,

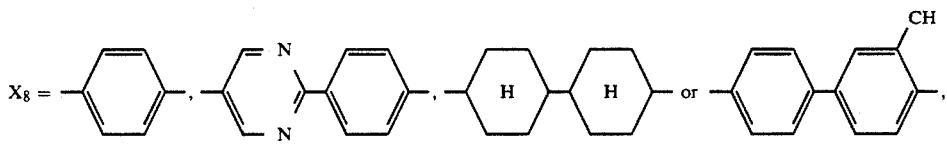

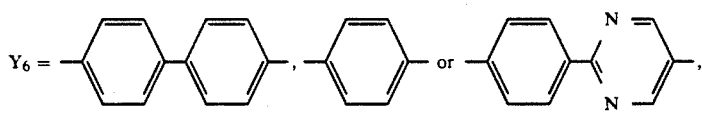

*$R_{12} = -CH_2*CHC_2H_5, -O*CHOC_3H_7, -OCH_2*CHC_2H_5, -O(CH_2)_5*CHOC_3H_7, -CO(CH_2)_2*CHC_2H_5$, (with CH₃ branches; fifth has O=C)

$-O*CHCOC_6H_{13}, -O(CH_2)_2*CHC_2H_5, -OCH_2*CHC_4H_9, -CH_2CH_2COCH_2*CHC_4H_9$ or $-OCH_2*CHC_6H_{13}$;

(with CH₃, Cl, F, O=C F, F branches)

$R_3'-X_9-CH_2O-Y_7-*R_{13}$ wherein $R_3' = C_{10}H_{21}O-$ or $C_nH_{2n+1}-$ (n = 4, 6, 7 or 8),

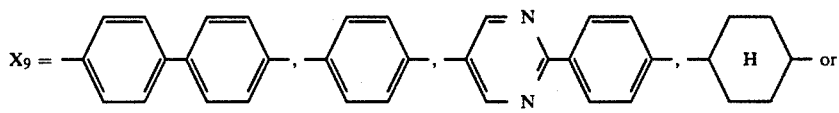

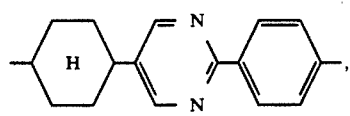

-continued $Y_7 =$ 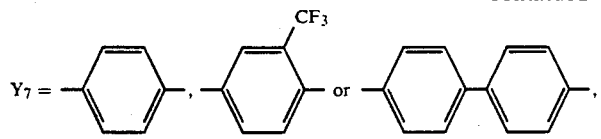

$*R_{13} =$ $-OCH_2*\overset{CH_3}{C}HC_2H_5$, $-OCH_2*\overset{CH_3}{C}HC_5H_{11}$, $-O(CH_2)_3*\overset{CH_3}{C}HC_5H_{11}$, $-O(CH_2)_3*\overset{CH_3}{C}HOC_5H_{11}$, $-O(CH_2)_2*\overset{CH_3}{C}HOC_3H_7$, $-O*\overset{CH_3}{C}HCH_2OC_2H_5$, $-OCH_2*\overset{CH_3}{C}HC_7H_{15}$, $-O*\overset{CH_3}{C}H\underset{O}{\overset{\parallel}{C}}OC_3H_7$, $-O*\overset{CH_3}{C}H\underset{O}{\overset{\parallel}{C}}OC_6H_{13}$, $-\overset{O}{\overset{\parallel}{C}}CH_2*\overset{CH_3}{C}HC_2H_5$, $-\overset{O}{\overset{\parallel}{C}}(CH_2)_2*\overset{CH_3}{C}HC_2H_5$, $-\overset{O}{\overset{\parallel}{O}}CCH_2*\overset{CH_3}{C}HC_2H_5$, $-\overset{O}{\overset{\parallel}{O}}CCH_2*\overset{CH_3}{C}HC_2H_5$, $-CH_2OCH_2*\overset{F}{C}HC_{10}H_{21}$, $-CH_2O\overset{O}{\overset{\parallel}{C}}*\overset{Cl}{C}HC_3H_7$, $-CH_2O\overset{O}{\overset{\parallel}{C}}CH_2*\overset{F}{C}HC_5H_{11}$ or $-(CH_2)_2O\overset{O}{\overset{\parallel}{C}}CH_2*\overset{Cl}{C}HC_2H_5$;

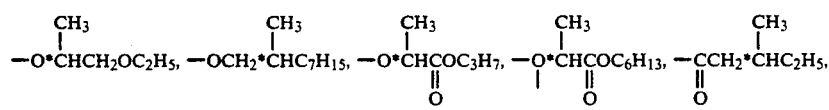

wherein n = 6 or 8, $X_{10} =$ 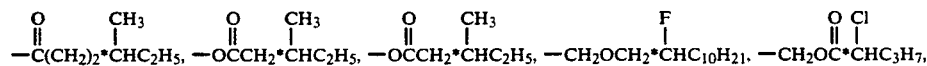;

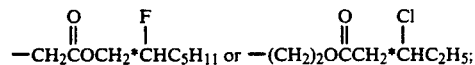

wherein $R_4' = -C_{10}H_{21}$, $-OC_{10}H_{21}$ or $-OC_8H_{17}$, $X_{11} =$ 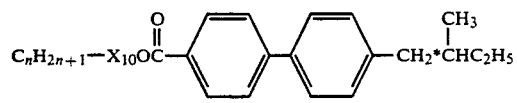, $*R_{14} = -*\overset{Cl}{C}HC_3H_7$, $-*\overset{Br}{C}HC_3H_7$, $-*\overset{F}{C}HC_8H_{17}$, $-CH_2*\overset{CF_3}{C}HC_4H_9$, $-*\overset{CH_3}{C}HOC_8H_{17}$ or $-(CH_2)_2*\overset{CH_3}{C}HOC_5H_{11}$;

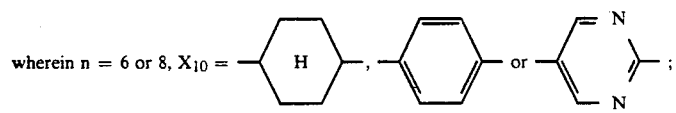

wherein n = 6 or 10, $X_{12} =$ 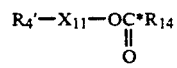, $Y_8 =$ 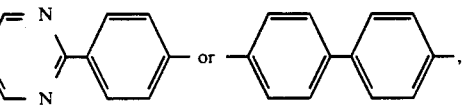, $*R_{15} = -CH_2*\overset{CH_3}{C}HOC_5H_{11}$, $-CH_2*\overset{CH_3}{C}HOC_8H_{17}$, $-CH_2*\overset{F}{C}HC_6H_{13}$ or $-CH_2*\overset{Cl}{C}HCH(CH_3)_2$;

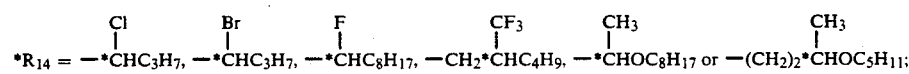

wherein n = 5 or 8, $X_{13} =$ 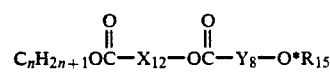,

Y_9 = 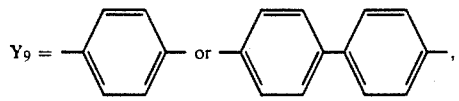
*R_16 = —(CH_2)_2*CHOC_5H_11 with CH_3 branch, or —*CHCOC_5H_11 with CH_3 branch and =O;
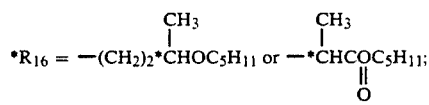
wherein Z_2 = —(CH_2)_2—, —CH_2CS— (=O) or —(CH_2)_2CO— (=O);
$C_nH_{2n+1}$—X_14—CO—Y_10—*R_17
       ‖
       O
wherein n = 8, 10, or 12, X_14 = 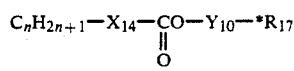
Y_10 = 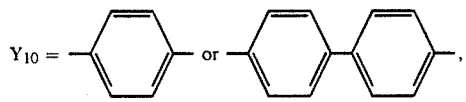
*R_17 = —CH_2*CHC_2H_5 (CH_3), —CH_2*CHC_6H_13 (F) or —OCO*CHC_2H_5 (Cl);
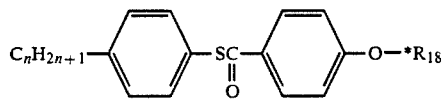
wherein n = 8 or 10, *R_18 = —CH_2*CHC_8H_17 (F) or —CH_2*CHC_3H_7 (CH_3);
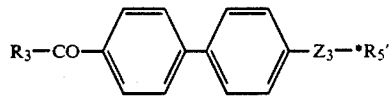
wherein R_3 = —C_8H_17 or —CHC_3H_7 (CH_3), Z_3 = —O— or —CO— (=O),
*R_5' = —CH_2*CHC_8H_17 (F) or —CH_2*CHCH(CH_3)_2 (Cl);
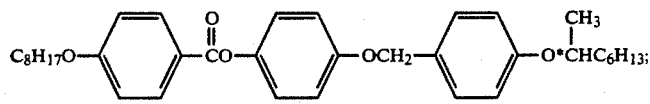
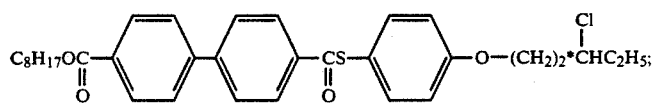
$C_mH_{2m+1}$—X_15—$C_nH_{2n+1}$

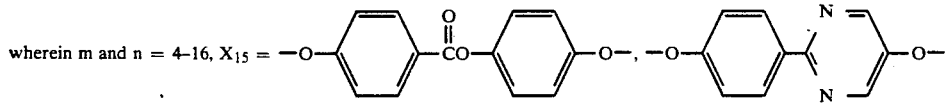

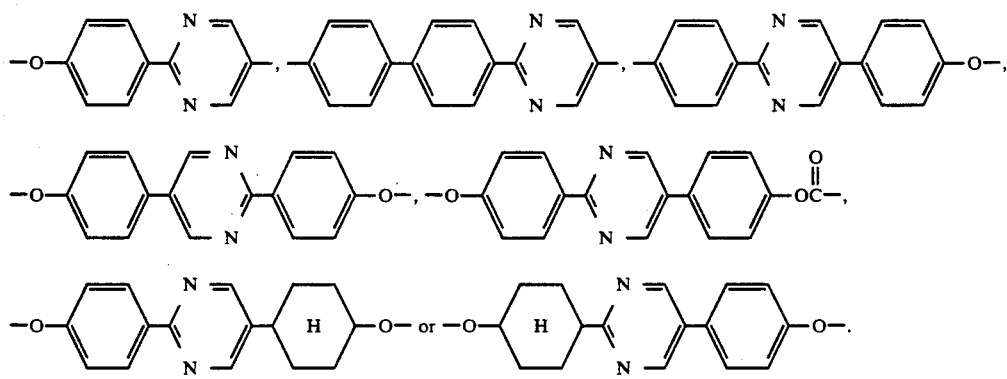

The present invention will now be described in detail with reference to the following examples.

REFERENTIAL EXAMPLE 1

Synthesis of t-butyl (S)-γ-butyrolactone-γ-carboxylate (S)-γ-butyrolactone-γ-carboxylic acid was synthesized according to the process of D. L. Coffec et al (J. Org. Chem., 1988, 53, pages 4780–4786). Namely, 147 g of L-glutamic acid was suspended in 500 ml of water, and 104 g of sodium nitrite dissolved in 144 ml of water and 250 ml of 5.6N hydrochloric acid were simultaneously added dropwise into the suspension with violent stirring over a period of more than 5 hours. During the dropwise addition, the reaction temperature was maintained at 15° to 20° C.

After the dropwise addition, water was removed by distillation under a reduced pressure while maintaining the temperature below 40° C., ethyl acetate was added to the residue, and the mixture was dried over magnesium sulfate.

The mixture was filtered, and 20 g of an acid type ion exchange resin (Amberlite R-120B) was added to the filtrate to remove the remaining glutamic acid. Then the mixture was filtered and the solvent removed under a reduced pressure, and the remaining water was removed by azeotropic distillation with benzene.

Methylene chloride was added to the residue, and crystallization was effected in a refrigerator to obtain 74 g of (S)-γ-butyrolactone-γ-carboxylic acid. The obtained compound was suspended in 200 ml of ether, 25 g of an acid type ion exchange resin (Amberlite IR-120B) was added to the suspension, the mixture was cooled to $-20°$ C., 60 ml (1.2 equivalents) of isobutylene was added to the mixture, and a reaction was carried out at 0° C. with stirring for 4 hours. After the reaction, the solid was removed by filtration, isobutylene and ether were distilled from the filtrate, and the residue was subjected to distillation under a reduced pressure to obtain t-butyl (S)-γ-byrolactone-γ-carboxylate [120° to 123° C./4 mmHg, $[α]_D$ (23.5° C.)= +4.81 (C=0.935, $CHCl_3$)].

REFERENTIAL EXAMPLE 2

Synthesis of (2S,5R)-2-hydroxy-5-(4-pentyloxyphenyl)-δ-valerolactone

In 10 ml of tetrahydrofuran was suspended 0.24 g of magnesium, and a solution of 2.45 g of p-bromophenol pentyl ether in 5 ml of dry tetrahydrofuran was added to the suspension in an argon atmosphere to synthesize a Grignard reagent.

Separately, a solution of 1.86 g of t-butyl (S)-γ-butylolactone-γ-carboxylate in 5 ml of dry tetrahydrofuran was prepared and charged in a thoroughly dried three-neck flask, the solution was cooled to $-20°$ C. in an argon atmosphere, and the above-mentioned Grignard reagent was added dropwise into the solution. The mixture was stirred for 3 hours, the temperature was returned to room temperature, and the mixture was stirred overnight. A saturated aqueous solution of ammonium chloride was added to the mixture, and the Grignard reaction product was extracted with ethyl acetate. The extract was washed with 10% sulfuric acid and then with water, dried over magnesium sulfate, and the precipitate was removed by filtration and the solvent was removed from the residual solution by distillation under a reduced pressure to obtain a crude product. The crude product was purified by the silica gel chromatography to obtain 2.4 g of t-butyl (2S)-2-hydroxy-5-(4-pentyloxyphenyl)-5-ketoheptanoate having the following properties.

$[α]_D$ (23° C.)= $-8.08$ (C=0.928, $CHCl_3$);
$IR_{neat}$=3400, 1730, 1600 $cm^{-1}$;
NMR (90 MHz, $CDCl_3$)=0.93 (3H, t), 1.50 (9H, s), 2.2–2.6 (2H, m), 2.98 (2H, t), 4.02 (2H, t), 4.78 (1H, m), 6.90 (2H, d), 7.94 (2H, d)

The obtained compound was dissolved in 10 ml of isopropanol, the solution was added dropwise in a suspension of 0.3 g of sodium boron hydride in 5 ml of isopropanol, and the mixture was stirred at room temperature overnight to effect reaction. A saturated aqueous solution of ammonium chloride was added to the mixture, the reaction product was extracted with chloroform, and the extract was washed with water and dried over magnesium sulfate. The solvent was removed under a reduced pressure. The obtained crude t-butyl (2S,5RS)-2-hydroxy-5-(4-methoxyphenyl)-heptanoate was dissolved in benzene, 0.1 g of p-toluenesulfonic acid was added to the solution, and a reaction was carried out at room temperature with stirring overnight. The obtained benzene solution was washed with an aqueous solution of sodium bicarbonate and then with water, dried over magnesium sulfate, the solvent was removed under a reduced pressure, and the obtained crude product was subjected to optical resolution by the silica gel column chromatography to obtain 0.6 g of (2S,5R)-2-hydroxy-5-(4-pentyloxyphenyl)-δ-valerolactone having the following properties.

IR$_{neat}$=3400, 1730, 1600 cm$^{-1}$;
NMR (90 MHz, CDCl$_3$)=0.92 (3H, t), 1.2–2.2 (10H, m), 4.30 (1H, m), 4.92 (1H, m), 6.88 (2H, d), 7.30 (2H, d).

REFERENTIAL EXAMPLE 3

Synthesis of (S)-4-bromo-1,2-butanediol acetonide

In 1.5 l of acetone was dissolved 81 g of (S)-1,2,4-butanetriol, 0.5 g of p-toluenesulfonic acid was added to the solution, and a reaction was carried out at room temperature with stirring overnight.

The thus obtained solution was neutralized with sodium bicarbonate, the precipitate was removed by filtration, and the filtrate was concentrated under a reduced pressure. The concentrate was subjected to distillation under a reduced pressure to obtain 86.5 g of (S)-1,2,4-butanetriol-1,2-acetonide as a fraction having a boiling point of 108° C. under 20 mmHg.

In 40 ml of methylene chloride were dissolved 29.2 g of the obtained acetonide and 99.5 g of carbon tetrabromide, and a methylene chloride solution of 52.3 g of triphenylphosphine was added dropwise into the solution over a period of 8 hours. The mixture was stirred at room temperature for 1 hour to effect reaction, 1.5 l of n-pentane was added to the mixture, the precipitate was removed by filtration, and the remaining n-pentane solution was washed with a saturated aqueous solution of sodium bicarbonate and then with water, and dried over magnesium sulfate. Then n-hexane was partially distilled off from the solution and the residue was concentrated, and the concentrate was subjected to distillation under a reduced pressure to obtain 23 g of (S)-4-bromo-1,2-butanediol acetonide as a fraction having a boiling point of 45° C. under 2 mmHg.

REFERENTIAL EXAMPLE 4

Synthesis of (2R,5S)-2-(4-benzyloxyphenyl)-5-hydroxymethyl-δ-valerolactone

In 2 ml of tetrahydrofuran was dissolved 1.01 g (10 millimoles) of diisopropyl amine, and 6.5 ml of 14.5% solution of n-butyl lithium in hexane was added to the solution to form lithium diisopropylamine. The solution was cooled to −20° C. and a solution of 1.21 g (5 millimoles) of 4-benzyloxyphenylacetic acid in 5 ml of tetrahydrofuran was added dropwise into the solution. Then 3 ml of hexamethyl phosphorictriamide was added to the mixture, and reaction was carried out at a temperature maintained at −5° to 0° C. with stirring for 30 minutes. The obtained di-anion solution was cooled to −30° C., and 2.3 g (9.6 millimoles) of (S)-4-bromo-1,2-butanediol acetonide was added dropwise into the solution. After the dropwise addition, the mixture was stirred for 2 hours at a temperature controlled to 10° to 20° C. Then, water was added to the mixture, tetrahydrofuran was removed by distillation, and the residue was neutralized with dilute hydrochloric acid. The reaction product was extracted from the solution with chloroform, and the extract was washed with water and dried over magnesium sulfate. The solvent was removed under a reduced pressure. The obtained product was purified by the silica gel column chromatography to obtain purified (2R,5S)-2-(4-benzyloxyphenyl)-5-hydroxymethyl-δ-valerolactone.

REFERENTIAL EXAMPLE 5

Synthesis of (2S,5R)-2-carboxy-5-hydroxymethyl-δ-valerolactone

To 40 g (1 mole) of 60% sodium hydride washed with dry pentane was added 300 ml of dry tetrahydrofuran, and a solution of 176 g (1.1 moles) of diethyl malonate in 350 ml of tetrahydrofuran was slowly added into the obtained suspension with stirring. After the dropwise addition, 20.7 g (0.1 mole) of (S)-4-bromo-1,2-butanediol acetonide was added into the mixture over a period of 2 hours. The mixture was stirred for 20 hours to effect reaction. Then acetic acid dissolved in ether was added to the mixture to neutralize the excessive alkali, ether was added to the mixture, and the mixture was washed with a saturated saline solution and dried over magnesium sulfate. The solvent was removed under a reduced pressure, and optical resolution was carried out by the silica gel column chromatography to obtain 5.5 g of (2S,5S)-2-carboxy-5-hydroxymethyl-δ-valerolactone.

EXAMPLE 1

Synthesis of (2R,5R)-2-(4-octyloxy)phenylcarboxy-5-(4-pentyloxyphenyl)-δ-valerolactone In 2 ml of benzene was dissolved 0.1 g of (2S,5R)-2-hydroxy-5-(4-pentyloxyphenyl)-δ-valerolactone, and 0.1 g of 4-octyloxybenzoic acid and 0.05 g of diethyl azodicarboxylate were added to the solution. Then 0.1 g of triphenylphosphine was added to the mixture and reaction was carried out by continuing stirring at room temperature overnight. The solvent was removed from the mixture by distillation and the obtained crude product was purified by the silica gel column chromatography to obtain 0.08 g of oily (2R,5S)-2-(4-octyloxy)-phenylcarboxy-5-(4-pentyloxyphenyl)-δ-valerolactone having the following properties.

IR$_{neat}$=1730, 1600 cm$^{-1}$;
NMR (90 MHz, CDCl$_3$)=0.90 (6H, dt), 1.2–2.4 (H, m), 3.93 (2H, t), 4.02 (2H, t), 4.42 (2H, m), 4.50 (1H, m), 5.00 (1H, m), 6.90 (4H, dd), 7.29 (2H, d), 8.02 (2H, d).

EXAMPLE 2

Synthesis of (2S,5S)-2-[4-(4-octyloxy)benzoyloxy]-phenyl-5-methyl-δ-valerolactone and (2R,5S)-2-[4-(4-octyloxy)benzoyloxy]phenyl-5-methyl-δ-valerolactone To a solution of 8 g of ethyl (S)-3-hydroxybutanoate and 6.2 g of imidazole in 40 ml of dimethylformamide was added 10.9 g of t-butyldimethylsilyl chloride at room temperature, the mixture was stirred for 12 hours, and the solution was poured into ice water and extracted with ether. The extract was washed with a saturated aqueous solution of sodium hydrogencarbonate, water and then a saturated aqueous solution of sodium chloride and dehydrated over magnesium sulfate, the solvent was removed by distillation, and the residue was subjected to distillation under a reduced pressure to obtain 11.8 g of ethyl (S)-3-t-butyldimethylsilyloxybutanoate. A solution of 9.8 g of the obtained compound in 20 ml of anhydrous ether was added dropwise into a suspension of 1.0 g of lithium borohydride in 100 ml of anhydrous ether at room temperature in an argon current, and then, 3.72 ml of a 1M solution of lithium triethylborohydride in tetrahydrofuran was added dropwise into the mixture. The mixture was refluxed for 3 hours, a saturated aqueous solution of ammonium chloride was added to the mixture, and the mixture was extracted with ether. The ether extract was washed with a saturated aqueous solution of sodium chloride and dehydrated on magnesium sulfate, the solvent was removed by filtration, and the residue was subjected to distillation under a reduced pressure to obtain 7.9 g of (S)-3-t-butyldimethylsilyloxy-1-butanol. A solution of 5.7 g of p-toluenesulfonyl chloride in 10 ml of pyridine was added dropwise into a solution of 5.4 g of the obtained compound in 8 ml of pyridine at 0° C., the mixture was stirred at 5° C. for 3 hours, a small amount of water was added to the mixture, and the mixture was stirred for 30 minutes. The solution was poured into a saturated aqueous solution of ammonium chloride and extracted with ether, the ether extract was washed with water, a saturated aqueous solution of copper sulfate, water and then a saturated aqueous solution of sodium chloride in order, and the solvent was removed by distillation. The residue was dissolved in 200 ml of acetone and 35 g of sodium iodide and 20 g of sodium hydrogencarbonate were added to the solution. The mixture was refluxed for 2 hours, concentrated, poured into ice water, and extracted with ether. The ether extract was washed with a 10% aqueous solution of sodium thiosulfate and then with a saturated aqueous solution of sodium chloride, and dehydrated over magnesium sulfate. The solvent was removed by distillation and the residue was purified by the silica gel column chromatography using hexane as the eluent to obtain 5.9 g of (S)-3-t-butylmethylsilyloxy-1-iodobutane. To a solution of 1.02 ml of diisopropylamine in 12 ml of anhydrous tetrahydrofuran was added 4.8 ml of a 1.58M solution of n-butyl lithium in hexane at −40° C. in an argon atmosphere, and the mixture was stirred for 20 minutes. Then, 12 ml of 1.5 g of methyl 4-methoxymethoxyphenylacetate in anhydrous tetrahydrofuran was added dropwise into the mixture at −78° C. over a period of 1 hour, and the mixture was stirred for 20 minutes. Then, a solution of 2.34 g of (S)-3-t-butylmethylsilyloxy-1-iodobutane and 1.3 g of hexamethylphosphoramide in 3 ml of tetrahydrofuran was added to the mixture. Then, the mixture was stirred at −40° C. for 3 hours, and an aqueous solution of ammonium chloride was added to the formed solution. The mixture was extracted with ether, and the ether extract was washed and dehydrated over magnesium sulfate. The solvent was removed by distillation and the residue was purified by the silica gel column chromatography using hexane/ethyl acetate as the eluent to obtain 1.8 g of methyl 2-(4′-methoxymethoxyphenyl-5-t-butyldimethylsilyloxy)hexanoate. In 3 ml of ethanol was dissolved 0.45 g of the obtained compound, and 3 ml of a 10% aqueous solution of sodium hydroxide was added to the solution, and the mixture was stirred for 12 hours. The pH value was adjusted to 3 and the mixture was extracted with methylene chloride. The extract was dissolved in 3 ml of tetrahydrofuran, 3 ml of 6N hydrochloric acid was added to the solution, the mixture was stirred at room temperature for 2 hours, and water was added to the mixture. Then, the mixture was extracted with chloroform, and the extract was washed with water and then with a saturated aqueous solution of sodium chloride. The solvent was removed by distillation, azeotropic dehydration was carried out with benzene, and the residue was purified by the silica gel column chromatography using dichloromethane/methanol as the developing solvent to obtain 0.16 g of (5S)-2-(4-hydroxyphenyl)-5-methyl-δ-valerolactone. Then, 72 mg of the obtained compound was dissolved in 2 ml of methylene chloride, and 87 mg of 4-octyloxybenzoic acid, 72 mg of N,N′-dicyclohexylcarbodiimide, and 13 mg of N,N-dimethylaminopyridine were added to the solution, and the mixture was stirred at room temperature for 16 hours. Insoluble substances were removed by filtration and the solvent was removed by distillation, and the residue was purified by the silica gel column chromatography using hexane/ether as the eluent to obtain 130 mg of (5S)-2-(4′-octyloxy-4-benzoyloxy)phenyl-5-methyl-δ-valerolactone. When the obtained compound was fractionated and purified by the high-speed liquid chromatography (HPLC), there were obtained (2S,5S)-2-(4′-octyloxy-4-benzoyloxy)phenyl-5-methyl-δ-valerolactone and (2R,5S)-2-(4′-octyloxy-4-benzoylox-y)phenyl-5-methyl-δ-valerolactone. These compounds showed the following phase transitions.

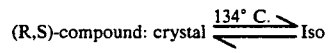

(R,S)-compound: crystal ⇌ 134° C. Iso

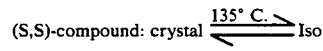

(S,S)-compound: crystal ⇌ 135° C. Iso

By repeating the above procedures in the same manner except that an ethyl ester of a β-hydroxy fatty acid having 5 to 21 carbon atoms instead of ethyl (S)-3-hydroxybutanoate, a derivative having an alkyl group having 2 to 18 carbon atoms at the 5-position of the δ-valerolactone ring was obtained. When the above procedures were repeated in the same manner except a 4-alkoxybenzoic acid having 1 to 7 or 9 to 18 carbon atoms in the alkoxy group, a 4-alkylbenzoic acid having 1 to 18 carbon atoms in the alkyl group, a 4-alkanoyloxybenzoic acid having a carboxyl group having 2 to 19 carbon atoms, a 4-alkoxybenzyl alcohol having 1 to 18 carbon atoms in the alkoxy groups, an alkylbenzyl alcohol having 1 to 18 carbon atoms in the alkyl group or a 4-alkanoyloxybenzyl alcohol having a carboxyl group having 2 to 19 carbon atoms was used instead of 4-octyloxybenzoic acid, there was obtained a derivative having, as the substituent attached to the phenyl group, a 4-(4-alkoxy)-benzoyloxy, 4-(4-alkoxy)-benzoyloxy, 4-(4-alkanoyloxy)-4-benzoyloxy, 4-(4-alkoxy)-benzyloxy, 4-(4-alkyl)-benzyloxy or 4-(4-alkanoyloxy)-benzyloxy group instead of the 4-(4-octyloxy)-benzoyloxy group.

Furthermore, when the above procedures were repeated in the same manner except that methyl 4-hydroxymethylphenylacetate was used instead of methyl 4-methoxyphenylacetate, and an alkoxyphenol having 1 to 18 carbon atoms in the alkoxy group, an alkylphenol having 1 to 18 carbon atoms in the alkyl group or a 4-alkanoyloxyphenol having a carboxyl group having 2 to 19 carbon atoms was used, there was obtained a derivative having, as the substituent to the phenyl group, a 4-(4-alkoxy)-phenyloxymethyl, 4-(4-alkyl)-phenyloxymethyl or 4-(4-alkanoyloxy)-phenyloxymethyl group instead of the 4'-octyloxy-4-benzoyloxy group.

When a 2-(4-hydroxymethylphenyl)-5-alkyl-δ-valerolactone synthesized by using methyl 4-hydroxymethylphenylacetate was oxidized in acetone by using a dilute sulfuric acid solution of chromic anhydride (Jones' reagent) to obtain a 2-(4-carboxyphenyl)-5-alkyl-δ-valerolactone and this compound was reacted with an alkylphenol having 1 to 18 carbon atoms in the alkyl group or an alkoxyphenol having 1 to 18 carbon atoms in the alkoxy group, a corresponding 2-[4-(4-alkoxy)phenoxycarbonyl]phenyl-5-alkyl-δ-valerolactone or 2-[4-(4-alkyl)phenoxycarbonyl]phenyl-5-alkyl-δ-valerolactone was synthesized.

EXAMPLE 3

Synthesis of (2R,5S)-2-butyl-5-(4'-octyloxybiphenyloxymethyl)-δ-valerolactone and (2S,5S)-2-butyl-5-(4'-octyloxybiphenyloxymethyl)-δ-valerolactone In 12 ml of anhydrous tetrahydrofuran (THF) was dissolved 1.02 ml of diisopropylamine, and 4.8 ml of a 1.58M solution of n-butyl lithium in hexane was added to the solution at −40° C. in an argon atmosphere, and the mixture was stirred for 20 minutes and cooled to −78° C. A solution of 0.92 g of methyl hexanoate in 12 ml of anhydrous THF was added dropwise into the mixture over a period of 1 hour. The mixture was stirred for 20 minutes, and about 3 ml of a solution of 1.0 g of (S)-4-iodobutane-1,2-glycolactonide synthesized from (S)-1,2,4-butanetriol and 1.3 g of hexamethylphosphoramide in THF was added to the mixture. Then, the mixture was stirred at −40° C. for 3 hours, a saturated aqueous solution of ammonium chloride was added to the mixture, the mixture was extracted with ether, and the ether extract was washed with water and dried over magnesium sulfate. The solvent was removed by distillation and the obtained crude product was purified by the silica gel column chromatography to obtain 0.9 g of methyl 2-butyl-5,6-dihydroxyhexanoate acetonide. The obtained compound was treated with 4N hydrochloric acid in a 1/1 mixed solvent of methanol/water and hydrolyzed with an equivalent amount of potassium hydroxide. The majority of methanol was removed by distillation, and the residual mixture was made acidic and extracted with chloroform. The chloroform extract was washed with water and dried over magnesium sulfate. The solvent was removed by distillation, the obtained crude product was dissolved in benzene, and a catalytic amount of p-TsOH was added to the solution. The solution was refluxed for 3 hours and cooled. Then, the benzene solution was washed with an aqueous solution of sodium hydrogen carbonate and a saturated aqueous solution of sodium chloride and dried, the solvent was removed by distillation, and the obtained crude product was purified by the silica gel column chromatography to obtain 0.4 g of (S)-2-butyl-5-hydroxymethyl-δ-valerolactone. The obtained compound was dissolved in 20 ml of benzene, 0.8 g of 4-(4'-octyloxy)biphenol was added to the solution, and 1 g of triphenylphosphine and 0.9 g of diethyl azodicarboxylate were further added. Reaction was carried out at room temperature overnight. The reaction product was concentrated under a reduced pressure and purified by the silica gel column chromatography to obtain 0.6 g of (2R,5S)-2-butyl-5-(4'-octyloxybiphenyloxymethyl)-δ-valerolactone. The obtained compound was fractionated and purified by HPLC to obtain 0.2 g of (2R,5S)-2-butyl-5-(4'-oxtyloxybiphenyloxymethyl)-δ-valerolactone and 0.2 g of (2S,5S)-2-butyl-5-(4'-octyloxybiphenyloxymethyl)-δ-valerolactone. These compounds showed the following phase transitions.

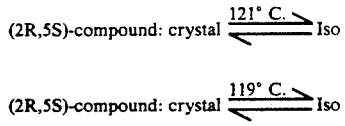

By repeating the above procedures in the same manner except that an ester of a linear or branched, saturated or unsaturated fatty acid having 3 to 21 carbon atoms was used instead of methyl hexanoate, a derivative having a linear or branched alkyl or alkenyl group having 1 to 19 carbon atoms at the 2-position of the δ-valerolactone ring instead of the butyl group was obtained.

When the above procedure were repeated in the same manner except that a 4-(4-alkoxy)benzoyloxyphenol, 4-(4-alkoxy)benzyloxyphenol, 4-(4-alkyl)benzoyloxyphenol, 4-(4-alkyl)benzyloxyphenol, 4-(4-alkanoyloxy)benzoyloxyphenol, 4-(4-alkanoyloxy)benzyloxyphenol, 4-(4-alkoxy)phenoxymethylphenol, 4-(4-alkyl)phenoxymethylphenol, 4-(4-alkanoyloxy)phenoxymethylphenol, 4-(4-alkyl)phenoxycarbonylphenol, 4-(4-alkoxy)phenoxycarbonylphenol or 4-(4-alkanoyloxy)phenoxycarbonylphenol having 1 to 18 carbon atoms in the alkoxy, alkyl or alkanoyl group was used instead of 4-(4'-octyloxy)-biphenol, a derivative having a 4-(4-alkoxy)-benzoyloxyphenoxy, 4-(4-alkoxy)benzyloxyphenoxy, 4-(4-alkyl)-benzoyloxyphenoxy, 4-(4-alkyl)-benzyloxyphenoxy, 4-(4-alkanoyloxy)benzoyloxyphenoxy, 4-(4-alkanoyloxy)benzyloxyphenoxy, 4-(4-alkoxy)phenoxymethylphenoxy, 4-(4-alkyl)phenoxymethylphenoxy, 4-(4-alkanoyloxy)phenoxymethylphenoxy, 4-(4-alkyl)phenoxycarbonylphenoxy, 4-(4-alkoxy)phenoxycarbonylphenoxy or 4-(4-alkanoyloxy)-phenoxycarbonylphenoxy group instead of 4'-octyloxybiphenyloxy group was synthesized.

EXAMPLE 4

Synthesis of (2R,5S)-2-butyl-5-(4'-octyloxybiphenyloxycarbonyl)-δ-valerolactone and (2S,5S)-2-butyl-5-(4'-octyloxybiphenyloxycarbonyl)-δ-valerolactone The (S)-2-butyl-5-hydroxymethyl-δ-valerolactone obtained in Example 2 was oxidized with pyridinium dichromate in dimethylformamide and the product was purified to obtain (S)-2-butyl-5-carboxyl-δ-valerolactone. In the same manner as described in Example 1, the obtained compound was esterified with 4-(4'-octyloxy)-biphenol by using diethyl azodicarboxylate and triphenylphosphine. The obtained product was purified by the silica gel column chromatography, and the obtained (2RS,5S)-2-butyl-5-(4'-octyloxybiphenyloxycarbonyl)-δ-valerolactone was further fractionated and purified by HPLC to obtain (2R,5S)-2-butyl-5-(4'-octyloxybiphenyloxycarbonyl))-δ-valerolactone and (2S,5S)-2-butyl-5-(4'-octyloxybiphenyloxycarbonyl)-67 -valerolactone. These compounds showed the following phase transitions.

(2S,5S) compound: crystal 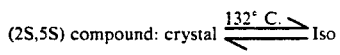 Iso (2R,5S) compound: crystal 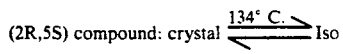 Iso By repeating the above procedures in the same manner except that an ester of a linear or branched, saturated or unsaturated fatty acid having 3 to 21 carbon atoms was used instead of methyl hexanoate, a derivative having a linear or branched alkyl or alkenyl group having 1 to 19 carbon atoms at the 2-position of the δ-valerolactone ring instead of the butyl group was obtained. When the above procedures were repeated in the same manner except that a 4-(4-alkoxy)benzoyloxyphenol, 4-(4-alkoxy)benzyloxyphenol, 4-(4-alkyl)benzoyloxyphenol, 4-(4-alkyl)benzyloxyphenol, 4-(4-alkanoyloxy)benzoyloxyphenol, 4-(4-alkanoyloxy)benzyloxyphenol, 4-(4-alkoxy)phenoxymethylphenol, 4-(4-alkyl)phenoxymethylphenol, 4-(4-alkanoloxy)phenoxymethylphenol, 4-(4-alkyl)phenoxycarbonylphenol, 4-(4-alkoxy)phenoxycarbonylphenol or 4-(4-alkanoyloxy)phenoxycarbonylphenol having 1 to 18 carbon atoms in the alkoxy, alkyl or alkanoyl group was used instead of 4'-octyloxybiphenol, a derivative having a 4-(4-alkoxy)benzoyloxyphenoxy, 4-(4-alkoxy)benzyloxyphenoxy, 4-(4-alkyl)benzoyloxyphenoxy, 4-(4-alkyl)benzyloxyphenoxy, 4-(4-alkanoyloxy)benzoyloxyphenoxy, 4-(4-alkanoyloxy)benzyloxyphenoxy, 4-(4-alkoxy)phenoxymethylphenoxy, 4-(4-alkyl)phenoxymethylphenoxy, 4-(4-alkanoyloxy)phenoxymethylphenoxy, 4-(4-alkyl)phenoxycarbonylphenoxy, 4-(4-alkoxy)phenoxycarbonylphenoxy or 4-(4-alkanoyloxy)phenoxycarbonylphenoxy group instead of 4'-octyloxybiphenyloxy group was synthesized.

EXAMPLE 5

Synthesis of (2R,5S)-2-butyl-5-[4-(4'-octyloxy)benzoyloxy]phenyl-δ-valerolactone 5-Keto-5-[4-(methoxy)phenyl]pentanoic acid obtained by Friedel-Crafts reaction between anisole and glutaric anhydride was reduced with baker's yeast to obtain (S)-5-(4-methoxyphenyl)-5-hydroxypentanoic acid. In the same manner as described in Example 3, the obtained compound was subjected to lactone-forming reaction in benzene by using p-TsOH as the catalyst to obtain (S)-5-(4-methoxy)phenyl-δ-valerolactone. The obtained lactone was butylated with butyl iodide by using lithium diisopropylamide in the same manner as described in Referential Example 4. The obtained crude product was purified by the silica gel column chromatography to obtain (2R,5S)-2-butyl-5-(4'-methoxyphenyl)-δ-valerolactone. The obtained compound was reacted with boron tribromide at −80° C. in methylene chloride, and the reaction mixture was stirred at room temperature overnight and treated with an alkali to obtain (2R,5S)-2-butyl-5-(4'-hydroxyphenyl)-δ-valerolactone. The obtained compound was reacted with 4-octyloxybenzoic acid by using DCC/DMAP as the dehydrating agent to obtain (2R,5S)-2-butyl-5-(4'-octyloxy-4-benzoyloxyphenyl)-δ-valerolactone. This compound showed the following phase transition.

crystal 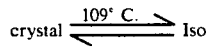 Iso

When the above procedures were repeated in the same manner except that a linear or branched alkyl iodide or bromide having 1 to 18 carbon atoms or a linear or branched alkenyl iodide or bromide having 2 to 18 carbon atoms was used instead of the butyl iodide, a derivative having a corresponding alkyl or alkenyl group at the 2-position of the δ-valerolactone ring instead of the butyl group was synthesized.

Furthermore, when the above procedures were repeated in the same manner except that a linear or branched alkoxybenzoic acid having 1 to 18 carbon atoms in the alkoxy group, a linear or branched alkenyloxybenzoic acid having 2 to 18 carbon atoms in the alkenyloxy group, a linear or branched alkanoyloxybenzoic acid having 2 to 18 carbon atoms in the alkanoyloxy group or a linear or branched alkyloxycarbonylbenzoic acid having 1 to 18 carbon atoms in the alkyl group was used instead of the 4-octyloxybenzoic acid, a derivative having a corresponding 4-alkoxy, 4-alkenyloxy, 4-alkanoyloxy or 4-alkyloxycarbonyl group instead of the 4-octyloxy group was synthesized.

Moreover, when the above procedures were repeated in the same manner except that a linear or branched 4'-alkoxybiphenyl having 1 to 18 carbon atoms in the alkoxy group was used instead of the anisole, a derivative having a (4'-alkoxy)biphenyloxy group instead of the (4'-octyloxy)benzoyloxy group was synthesized.

EXAMPLE 6

Synthesis or (2S,5R)-2-(4'-octyloxy)biphenyloxymethyl-5-methyl-δ-valerolactone

In 10 ml of DMF was dissolved 1.2 g of methyl (R)-β-hydroxybutyrate, and 1.8 g of t-butyldimethylsilyl chloride and 1.0 g of imidazole were added to the solution and reaction was carried out at room temperature overnight. Water was added to the solution and the mixture was extracted with ether. The extract was subjected to distillation to obtain 2 g of methyl (R)-β-t-butyldimethylsilyloxybutyrate. The obtained compound was dissolved in anhydrous ether and the solution was added dropwise into a suspension of 0.5 g of lithium aluminum hydride in anhydrous ether. After the dropwise addition, the mixture was refluxed for 3 hours. After the reaction, 0.5 ml of water, 0.5 ml of 15% NaOH and 1.5 ml of water were added in turn to the reaction mixture, 20 ml of THF was further added, and the mixture was stirred for 30 minutes. The precipitate was removed by filtration, and the filtrate was dried over magnesium sulfate and concentrated under a reduced pressure. The residue was subjected to distillation under reduced pressure to obtain (R)-3-t-butyldimethylsilyloxybutanol-1. The obtained compound was tosylated with p-tosyl chloride in pyridine. The obtained crude tosylate was treated with an excessive amount of sodium iodide in acetone, and insoluble substances were removed by filtration and the filtrate was concentrated and subjected to distillation under a reduced pressure to obtain (R)-1-iodo-3-t-butyldimethylsilyloxybutane. A solution of 3 g of diethyl malonate in 5 ml of THF was added dropwise into a suspension of 0.05 g of sodium hydride in THF. After the dropwise addition, the mixture was stirred at room temperature for 30 minutes, and a solution of 0.65 g of (R)-1-iodo-3-t-butyldimethylsilyloxybutane in THF was added to the mixture. Then, the mixture was stirred at room temperature overnight, water was added to the mixture, and the majority of THF was removed by distillation. The residue was extracted with ether, and the ether extract was washed with dilute hydrochloric acid and then with water and dried over magnesium sulfate. The solvent was removed by distillation and the residue was subjected to distillation under a reduced pressure to obtain diethyl (R)-3-t-butyldimethylsilyloxybutylmalonate. The obtained compound was dissolved in 10 ml of THF and 2 ml of a 1M solution of tetrabutyl ammonium fluoride in THF was added to the solution, and the mixture was stirred at room temperature overnight and concentrated under a reduced pressure. Water was added to the concentrate and the mixture was extracted with ether. The ether extract was washed with water and dried over magnesium sulfate. Ether was removed by distillation, the residue was dissolved in benzene, p-TsOH was added to the solution and the mixture was refluxed for 5 hours. The reacted solution was washed with an aqueous solution of sodium hydrogen carbonate and dried, the solvent was removed by distillation, and the residue was purified by the silica gel column chromatography to obtain (2RS,5R)-2-ethoxycarbonyl-5-methyl-δ-valerolactone. The obtained compound was reduced with sodium borohydride to obtain (2RS,5R)-2-hydroxymethyl-5-methyl-δ-valerolactone. In the same manner as described in Example 1, the obtained compound was reacted with 4-(4'-octyloxy)biphenol by using triphenylphosphine and diethyl azodicarboxylate. The reacted solution was purified by the silica gel column chromatography to obtain (2RS,5R)-2-(4'-octyloxybiphenyl)oxymethyl-5-methyl-δ-valerolactone. The obtained product was further fractionated and purified by HPLC to obtain (2R,5R)-2-(4'-octyloxybiphenyl)oxymethyl-5-methyl-δ-valerolactone and (2S,5R)-2-(4'-octyloxybiphenyl)-oxymethyl-5-methyl-δ-valerolactone. They showed the following phase transitions.

(2R, 5R) compound: crystal $\underset{\longleftarrow}{\overset{128° C.}{\longrightarrow}}$ Iso (2S, 5R) compound: crystal $\underset{\longleftarrow}{\overset{126° C.}{\longrightarrow}}$ Iso

EXAMPLE 7

A liquid crystal composition was obtained by mixing the following compounds at the following mixing ratio:

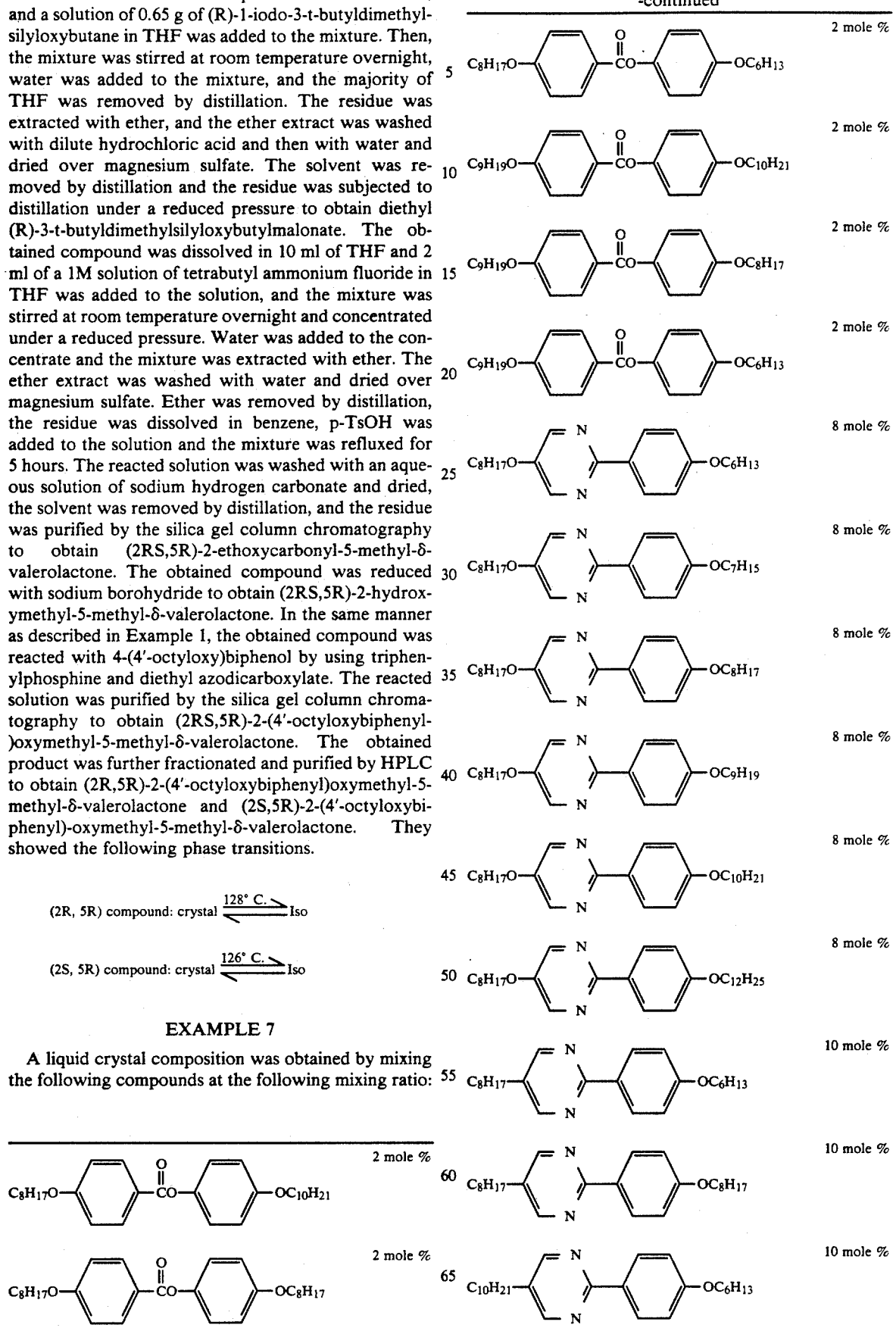

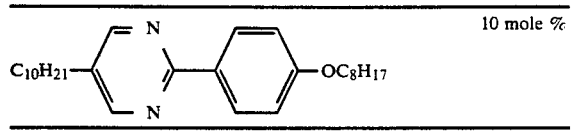

10 mole %

This composition showed the following phase transition:

In the above expression, Cryst represents the crystal, SmC represents the smectic C phase, N represents the nematic phase, and each number given in the vicinity of the arrow shows the transition temperature (°C.) to the corresponding phase.

Since this liquid crystal composition was composed solely of non-chiral compounds, the liquid crystal composition was not a ferroelectric liquid crystal and did not show a spontaneous polarization.

The ferroelectric liquid crystal composition obtained by mixing 98 mole % of the above composition with 2 mole % of the optically active compound obtained in Example 1 showed the Sm*C phase at temperatures from room temperature to 57° C., showed the SmA phase at 57° to 71° C., showed the chiral nematic phase at 71° to 76° C., and showed the isotropic phase at higher temperatures.

A liquid crystal element was prepared by casting the above composition in a cell having a thickness of 2 μm, which was provided with a transparent electrode layer and a parallel-rubbed polyimide layer on the surface of the electrode layer. The liquid crystal element was arranged between two orthogonally crossing polarizers, and an electric field was applied thereto. It was found that the intensity of the transmitted light was changed by application of a voltage of ±20 V. When the response time was determined from this change, it was found that the response time at 50° C. was 40μ sec.

EXAMPLE 8

A ferroelectric liquid crystal composition was prepared by mixing 98 mole % of the same non-chiral liquid crystal composition as used in Example 7 with 2 mole % of (2S,5S)-2-(4'-octyloxy-4-benzoyloxy)phenyl-5-methyl-δ-valerolactone obtained in Example 2. This ferroelectric liquid crystal composition showed the Sm*C phase at temperatures from room temperature to 61° C., showed the SmA phase at 61° to 66° C., showed the chiral nematic phase at 66° to 76° C., and showed the isotropic phase at higher temperatures.

The above composition was cast in the same cell having a thickness of 2 μm as that used in Example 7, whereby a liquid crystal element was prepared. The liquid crystal element exhibited a response time of 200μ sec at 25° C.

As apparent from the foregoing description, among the optically active compounds of the present invention, those which have liquid crystalline characteristics, show a high spontaneous polarization as a ferroelectric liquid crystal, are not colored, have a good chemical stability characteristics such as hydrolysis resistance, and have a good light stability. Furthermore, optically active compounds of the present invention, which have no liquid crystalline characteristics, are advantageous in that, if the compounds, are incorporated in a non-ferroelectric liquid crystal composition to form a ferroelectric liquid crystal composition or are incorporated as an additive in a ferroelectric liquid crystal composition, a liquid crystal composition having an enhanced spontaneous polarization and an improved response speed are obtained without causing coloration or a degradation of the chemical stability or light stability. Thus, a liquid crystal composition having good performances can be provided according to the present invention.

We claim:

1. A ferroelectric liquid crystal composition comprising:

(A) an optically active compound having δ-valerolactone ring, which is represented by the following general formula (1):

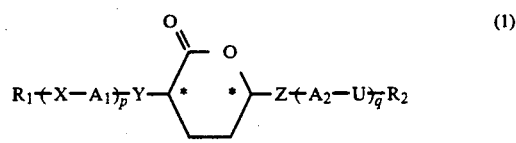

(1)

wherein $R_1$ and $R_2$ independently represent a linear or branched alkyl group having 1 to 18 carbon atoms, a linear or branched alkenyl group having 2 to 18 carbon atoms, a liner or branched alkoxyalkyl group having 1 to 3 carbon atoms in the alkoxy portion and 1 to 18 carbon atoms in the alkyl portion, or an alkyl, alkenyl or alkoxyalkyl group as mentioned above in which at least one hydrogen atom is substituted by a halogen atom, with the proviso that when $R_1$ or $R_2$ has a structure that can possess an optically active group, it may be an optically active group or a racemic modification, X is a direct bond, Y is a direct bond, U represents a direct bond, —O—,

is a direct bond, Z is —CH$_2$O—, $A_1$ and $A_2$ independently represent

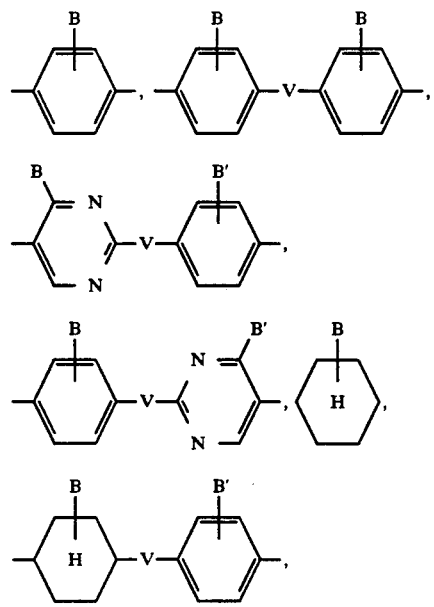

-continued

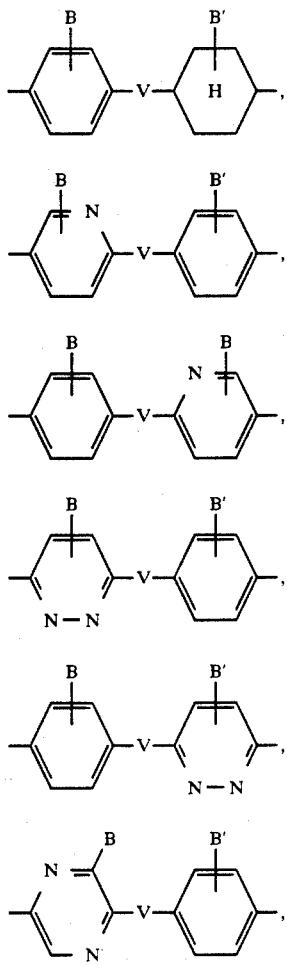

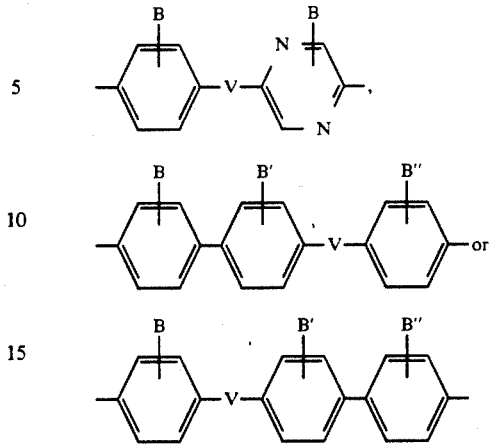

in which B, B' and B" independently represent a hydrogen atom, a halogen atom, a cyano group, a methyl group, a methoxy group or a trihalomethyl group and V represents a direct bond, —CH$_2$O—, —OCH$_2$—,

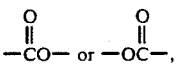

p is zero, q is one, and *C represents an asymmetric carbon atom; and (B) a material selected from the group consisting of ferroelectric liquid crystal compound, ferroelectric liquid crystal compositions, non-chiral liquid crystal compounds, a liquid crystal composition showing the phase series of isotropic phase-neumatic phase-smectic A phase, and a liquid crystal composition showing the phase series of isotropic phase-nematic phase-smectic C phase.

* * * * *